US009265914B2

(12) United States Patent
Fulton, III et al.

(10) Patent No.: US 9,265,914 B2
(45) Date of Patent: Feb. 23, 2016

(54) RECOVERY CATHETER ASSEMBLY

(71) Applicant: NFUSION VASCULAR SYSTEMS, LLC, Grand Junction, CO (US)

(72) Inventors: Richard Eustis Fulton, III, Grand Junction, CO (US); Richard Lotti, Santa Cruz, CA (US)

(73) Assignee: NFUSION VASCULAR SYSTEMS, LLC, Grand Junction, CO (US)

( * ) Notice: Subject to any disclaimer, the term of this patent is extended or adjusted under 35 U.S.C. 154(b) by 32 days.

(21) Appl. No.: 14/172,534

(22) Filed: Feb. 4, 2014

(65) Prior Publication Data

US 2014/0155815 A1 Jun. 5, 2014

Related U.S. Application Data

(63) Continuation of application No. 13/041,102, filed on Mar. 4, 2011.

(60) Provisional application No. 61/339,548, filed on Mar. 6, 2010, provisional application No. 61/341,587, filed on Apr. 1, 2010, provisional application No. 61/459,164, filed on Dec. 8, 2010.

(51) Int. Cl.
*A61B 17/12* (2006.01)
*A61B 5/0215* (2006.01)
(Continued)

(52) U.S. Cl.
CPC ...... *A61M 25/0074* (2013.01); *A61B 17/12036* (2013.01); *A61B 17/12045* (2013.01);
(Continued)

(58) Field of Classification Search
CPC ............... A61M 2025/1052; A61M 25/1011; A61M 25/1002; A61M 2025/105; A61M 25/0074; A61M 1/3615; A61M 1/367; A61M 25/0082; A61M 25/04; A61M 1/101; A61M 1/34; A61M 1/3619; A61M 25/007; A61M 2025/1097; A61B 17/12036; A61B 17/12045; A61B 17/12109; A61B 17/121; A61B 17/12136; A61B 17/12172; A61B 5/02152; A61B 2019/465; A61F 2/013
USPC .................. 604/96.01, 164.01, 523, 104–109
See application file for complete search history.

(56) References Cited

U.S. PATENT DOCUMENTS

| 5,069,662 A | 12/1991 | Bodden |
| 5,366,504 A | 11/1994 | Andersen et al. |

(Continued)

FOREIGN PATENT DOCUMENTS

| WO | 96/17645 | 6/1996 |
| WO | 99/42044 | 8/1999 |

(Continued)

OTHER PUBLICATIONS

International Search Report of the International Searching Authority for PCT/US2011/027254 dated Jun. 7, 2011.

(Continued)

*Primary Examiner* — Emily Schmidt
*Assistant Examiner* — Lauren M Peng
(74) *Attorney, Agent, or Firm* — Morgan Lewis & Bockius

(57) ABSTRACT

An example of recovery catheter assembly comprises an actuator element and a mechanically radially expandable and contractible recovery device operably connected to the actuator element. The recovery device has proximal and distal blocking portions and a central portion therebetween. The recovery device is at least partially placeable in a first, radially collapsed configuration and in a second, radially expanded configuration by manipulation of the actuator element. When in the second, radially expanded configuration, the proximal and distal blocking portions have radial dimensions greater than the radial dimension of the central portion thereby at least partially defining a collection chamber at the central portion.

14 Claims, 12 Drawing Sheets

(51) Int. Cl.

| | |
|---|---|
| *A61B 19/00* | (2006.01) |
| *A61M 25/00* | (2006.01) |
| *A61M 1/36* | (2006.01) |
| *A61M 25/04* | (2006.01) |
| *A61M 1/10* | (2006.01) |
| *A61M 1/34* | (2006.01) |
| *A61M 25/10* | (2013.01) |
| *A61F 2/01* | (2006.01) |

(52) U.S. Cl.
CPC ..... *A61B17/12109* (2013.01); *A61B 17/12136* (2013.01); *A61B 17/12168* (2013.01); *A61B 17/12172* (2013.01); *A61M 1/367* (2013.01); *A61M 1/3615* (2014.02); *A61M 25/0082* (2013.01); *A61M 25/04* (2013.01); *A61B 5/02152* (2013.01); *A61B 2019/465* (2013.01); *A61F 2/013* (2013.01); *A61M 1/101* (2013.01); *A61M 1/34* (2013.01); *A61M 1/3679* (2013.01); *A61M 25/007* (2013.01); *A61M 25/1011* (2013.01); *A61M 2025/1052* (2013.01); *A61M 2025/1097* (2013.01)

(56) References Cited

U.S. PATENT DOCUMENTS

| | | | |
|---|---|---|---|
| 5,470,314 A | 11/1995 | Walinsky | |
| 5,554,119 A | 9/1996 | Harrison et al. | |
| 5,558,642 A * | 9/1996 | Schweich et al. | 604/103.01 |
| 5,700,242 A | 12/1997 | Mulder | |
| 5,817,046 A | 10/1998 | Glickman | |
| 5,893,841 A | 4/1999 | Glickman | |
| 5,897,533 A | 4/1999 | Glickman | |
| 5,919,163 A | 7/1999 | Glickman | |
| 6,139,517 A | 10/2000 | Macoviak et al. | |
| 6,165,196 A | 12/2000 | Stack et al. | |
| 6,183,492 B1 | 2/2001 | Hart et al. | |
| 6,254,563 B1 | 7/2001 | Macoviak et al. | |
| 6,635,068 B1 * | 10/2003 | Dubrul et al. | 606/200 |
| 7,022,097 B2 | 4/2006 | Glickman | |
| 7,645,259 B2 | 1/2010 | Goldman | |
| 2007/0055299 A1 | 3/2007 | Ishimaru et al. | |
| 2007/0282303 A1 | 12/2007 | Nash et al. | |
| 2008/0015628 A1 | 1/2008 | Dubrul et al. | |
| 2008/0103573 A1 | 5/2008 | Gerber | |
| 2009/0018526 A1 | 1/2009 | Power et al. | |
| 2009/0112184 A1 | 4/2009 | Fierens et al. | |
| 2009/0131785 A1 | 5/2009 | Lee et al. | |

FOREIGN PATENT DOCUMENTS

| | | |
|---|---|---|
| WO | 2007/107327 | 9/2007 |
| WO | 2009/010962 | 1/2009 |

OTHER PUBLICATIONS

Written Opinion of the International Searching Authority for PCT/US2011/027254 dated Jun. 7, 2011.

* cited by examiner

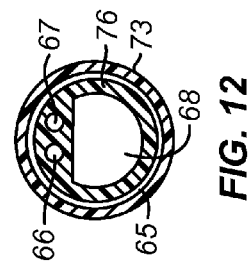
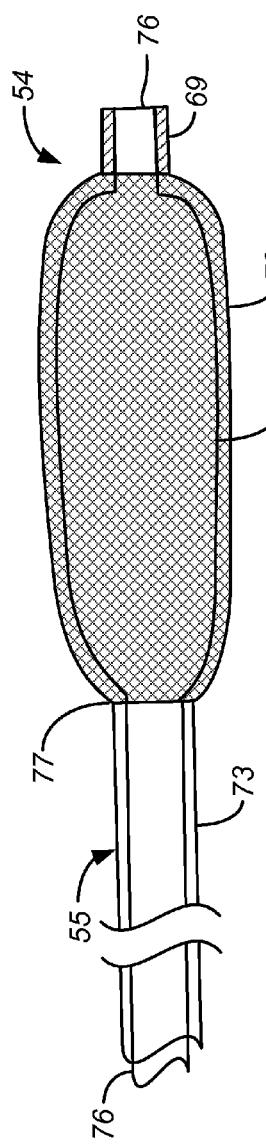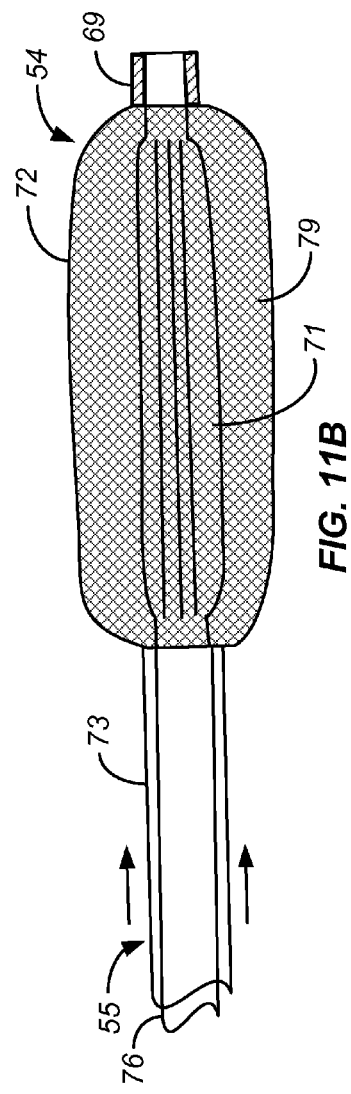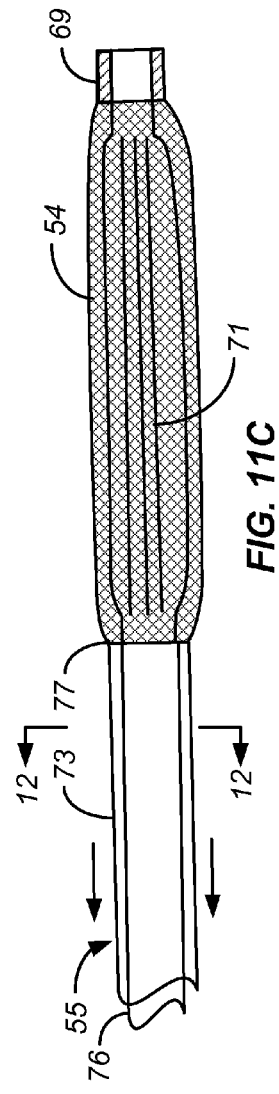

RECOVERY CATHETER ASSEMBLY

CROSS-REFERENCE TO RELATED APPLICATIONS

This application is a continuation application of U.S. application Ser. No. 13/041,102, filed Mar. 4, 2011, which claims priority benefit under 35 U.S.C. §119(e) to U.S. provisional application No. 61/339,548, filed Mar. 6, 2010; U.S. provisional application No. 61/341,587, filed Apr. 1, 2010; and U.S. provisional application No. 61/459,164, filed Dec. 8, 2010. The disclosure of the aforementioned patent applications U.S. application Ser. No. 13/041,102, U.S. provisional application No. 61/339,548, U.S. provisional application No. 61/341,587, and U.S. provisional application No. 61/459,164 are hereby incorporated by reference.

BACKGROUND OF THE INVENTION

1. Field of the Invention

The present invention relates to systems and methods of local organ perfusion of tumors or other serious conditions with one or more high dose treatment substances, isolating the venous outflow, collecting it, filtering it, and returning it to the body after removing the high dose treatment substance(s).

2. Description of Background Art

There are several methods of treating cancerous tumors including surgery, chemotherapy, focal ablation by delivery of various forms of energy, radiation, amongst others. Often, tumors are not resectable by surgery because they have spread into the surrounding tissues or to distant tissues such as the liver, lung, or brain. The treatment of metastatic disease to these organs is done with chemotherapy, focal surgical resection and focal ablation when there are only a few lesions, and occasionally with radiation. Oftentimes, the metastatic disease is diffuse and not amenable to surgery, radiation or focal ablation. This leaves chemotherapy as the only alternative, and the effectiveness of the chemotherapy is limited by the systemic toxicities cause by the drug including bone marrow suppression, neutropenia, nausea, diarrhea, anorexia, wasting, cachexia, bacterial or viral overgrowth amongst others.

A system, process, and method of isolated perfusion of organs with a very high dose of a chemotherapeutic agent, collection of the effluent venous blood from that organ before it enters the systemic circulation, filtering the chemotherapeutic agent from the collected blood, and returning the filtered blood without the chemotherapeutic agent to the systemic circulation has been described by Glickman in U.S. Pat. Nos. 5,817,046, 5,893,841, 5,897,533, 5,919,163, and 7,022,097 and by Bodden in U.S. Pat. No. 5,069,662. This system is currently marketed by Delcath, Inc., of New York, N.Y., as the Percutaneous Hepatic Perfusion (PHP) apparatus for the purpose of treating metastatic disease and primary tumors of the liver. In essence, a very high dose of a chemotherapeutic agent is infused into the hepatic artery over a period of time, usually from 30 minutes to an hour. The high dose chemotherapeutic agent perfuses the liver and is much more effective than a traditional systemic dose administered intravenously. This drug is taken up by the tumor and the remainder flows into the hepatic veins, which are a series of veins that drain from the liver into the upper inferior vena cava (IVC.) This blood which still contains toxic levels of the chemotherapeutic agent is collected by an isolation device which is part of this special apparatus (PHP). The hepatic venous blood isolation device is a double balloon system that is deployed in the inferior vena cava, the balloons being inflated above and below the hepatic veins, the hepatic venous effluent collected into a catheter and pumped through a filter outside the body that removes the chemotherapeutic agent, and returned to the superior vena cava via another catheter. A through return lumen, also referred to as a return channel, is provided to allow blood in the inferior vena cava from the lower body and kidneys to flow back to the heart while the balloons are occluding the vena cava.

While the current prior art apparatus is effective in treating the tumor or tumors of the liver, it is somewhat cumbersome to use, as the double balloons may occlude the renal and/or adrenal veins, and the balloons tend to occupy more space in the inferior vena cava than is desirable. Moreover, the through lumen that transmits blood from the lower inferior vena cava to the heart is not large enough to accommodate the volume of blood returning to the heart. This frequently results in a sudden drop in the patient's blood pressure, and occasionally a shock like condition. Since it is expected that the patient will need at least some level of resuscitation, an anesthesiologist is in attendance to deal with these problems. Obviously, the risk to the patient and the cost of the procedure increases dramatically because these problems with the prior art technology. This is significant, not only from the risk to the patient, but also because it may prevent interventionalists from pursuing this strategy of treatment for their patients and their referring physicians. There is the risk that these problems with the prior art device and technology may prevent this very effective system of therapy from being fully adopted by the medical community, thereby depriving thousands of patients who would have benefited from the therapy otherwise. There are significant problems that can result from these iatrogenically created complications such as renal and adrenal vein thrombosis, unstable perfusion of the heart, brain, and kidneys, resulting in heart attack, stroke, kidney damage amongst other complications, in a patient who is already compromised because of the underlying malignancy. These complications are the result of the use of the primitive balloon technology and method of occluding, altering, or re-directing blood flow in the human body.

The balloons of the prior art device limit the size of the through lumen as the expanded balloons must occupy most of the inferior vena cava to effectively isolate the hepatic veins. This limits the amount of blood that can be returned from the inferior vena cava to the right atrium, resulting in the problems noted in the above paragraph. The footprint of the expanded balloons, especially the caudal balloon, in the inferior vena cava is problematic as the distance between the more caudal hepatic veins and the renal/adrenal veins is frequently less than the footprint of the expanded balloon.

In reviewing a series of over 50 CT scans of the abdomen, the inventor has determined from measurements of the cavoatrial junction to the orifice of the left renal vein that the current prior art device of Glickman is likely to partially occlude the left renal vein in greater than ⅓ of the cases. If a 15 mm compensating factor is utilized for curvature and other measurement inaccuracies, then there would likely still be greater than 20% of cases in which the left renal vein would be at least partially covered by the caudal balloon of the current device.

Also, different diameter devices may be needed as measurement of the anteroposterior (AP) and transverse dimensions of the IVC revealed a great variation in those measurements. Average AP and transverse dimensions in the upper IVC, mid retrohepatic IVC and immediate supra renal vein IVC were 23.6 mm and 30.4 mm, 20.0 mm and 22.7 mm, and 20.2 mm and 28.3 mm, respectively. A minimal AP dimension of only 8 mm was present in one subject while a maximum AP dimension of 36 mm occurred in another subject.

Transverse dimensions varied from 10.2 mm to 40 mm in different subjects. The measurements taken may not apply to populations of different ethnicity and may vary even more in those different populations and age groups. Moreover, within the same patient, the IVC measurements many times revealed a large oblong supradiaphragmatic IVC, a smaller more rounded mid retrohepatic IVC, and a tilted, oblong configuration of the IVC just above the renal veins. In fact, the tilted oblong configuration just above the renal veins was frequently tilted in the opposite direction from the tilted oblong configuration of the supradiaphragmatic IVC.

SUMMARY OF THE INVENTION

Examples of the present invention will successfully and effectively collect the hepatic venous effluent, isolating it from the systemic circulation without the problems caused by the current double balloon system. According to some examples, isolation will occur without blockage of adrenal or renal veins while providing a large channel for blood to flow unimpeded from the inferior vena cava to the heart without the use of balloons.

A first example of recovery catheter assembly comprises an actuator element and a mechanically radially expandable and contractible recovery device operably connected to the actuator element. The recovery device has proximal and distal ends and comprises proximal and distal blocking portions at the proximal and distal ends thereof. The recovery device also has a central portion between the proximal and distal blocking portions. The recovery device is at least partially placeable in a first, radially collapsed configuration and in a second, radially expanded configuration by manipulation of the actuator element. When in the second, radially expanded configuration, the proximal and distal blocking portions have radial dimensions greater than the radial dimension of the central portion thereby at least partially defining a collection chamber at the central portion. In some examples the recovery device is fully placeable in the first, radially collapsed configuration and in the second, radially expanded configuration by manipulation of the actuator element. In some examples the recovery device comprises proximal and distal toroidal blocking balloons at the proximal and distal ends of the recovery device. Some examples include a hollow recovery catheter having a sidewall and defining a recovery lumen. Some examples may further comprise a lateral passageway extending through the central portion of the recovery device and the sidewall of the recovery catheter, the parts of the proximal and distal blocking portions and the central portion at least partially defining the collection chamber being liquid impervious with the exception of the passageway, whereby liquid in the collection chamber can pass through the passageway and into and through the recovery lumen. In some examples the recovery catheter comprises proximal, intermediate and distal portions, the lateral passageway is located along the intermediate portion of the recovery catheter, a blood pump is located along the distal portion of the recovery catheter, and a filter element is located along the distal portion of the recovery catheter for filtering out at least one agent from fluid flow through the recovery catheter lumen. In some examples a first pressure sensor is at the collection chamber, a second pressure sensor is positioned distal of the recovery device, a filter element and a pump are operably coupled to the recovery catheter to pump fluid through the recovery catheter and filter fluid passing through the recovery catheter, and the pump is operably coupled to the first and second pressure sensors to permit control of the pressure within the collection chamber during use. In some examples a filter element and a pump are operably coupled to the recovery catheter to pump fluid through the recovery catheter and filter fluid passing through the recovery catheter, a pressure sensor is located proximal to the pump, and the pump is operably coupled to the pressure sensor to permit control of the pressure within the collection chamber during use. In some examples the actuator element comprises first and second actuator elements, the recovery device comprises a proximal end operably connected to the first actuator element and a distal end operably connected to the second actuator element; the recovery device is at least partially placeable in the first, radially collapsed configuration and in the second, radially expanded configuration by manipulation of the first and second actuator elements.

A second example of a recovery catheter assembly, for use within a body passageway at an ostium, includes an outer, actuator sheath having a distal portion and an inner, hollow recovery catheter having a sidewall. The recovery catheter defines a recovery lumen and has a distal end. The recovery catheter is housed within the actuator sheath. An actuator wire extends along the recovery catheter and has a tip positioned distal of the distal end of the recovery catheter. A mechanically radially expandable and contractible recovery device has a proximal end secured to the distal portion of the actuator sheath by a proximal extension element and a distal end secured to the tip of the actuator wire by a distal extension element. The recovery device comprises proximal and distal blocking portions at the proximal and distal ends thereof, a central portion between the proximal and distal blocking portions, and a return lumen extending between the proximal and distal ends thereof. The recovery device is placeable in a first, radially collapsed configuration when the actuator wire is pushed distally to a distal actuator wire position relative to the recovery device and the actuator sheath is pulled proximally to a proximal actuator sheath position relative to the recovery device. The recovery device is placeable in a second, radially expanded configuration when the actuator wire is pulled proximally to a proximal actuator wire position relative to the recovery device and the actuator sheath is pushed distally to a distal actuator sheath position relative to the recovery device. When in the second, radially expanded configuration, the proximal and distal blocking portions have radial dimensions greater than the radial dimension of the central portion thereby defining a collection chamber at the central portion, and the proximal and distal expansion elements have open regions to permit fluid flow through the return lumen of the recovery device. A lateral passageway extends through the central portion of the recovery device and the sidewall of the recovery catheter. The parts of the proximal and distal blocking portions and the central portion defining the collection chamber are liquid impervious with the exception of the passageway, whereby liquid from an ostium of a liquid transporting vessel opening into the collection chamber can pass through the passageway and into and through the recovery lumen.

A third example of a recovery catheter assembly, for use within a body passageway at an ostium, comprises an outer, actuator sheath having a distal portion and an inner, hollow recovery catheter having a sidewall. The recovery catheter defines a recovery lumen and a distal end. The recovery catheter is housed within the actuator sheath. The recovery catheter has an actuator wire extending along the recovery catheter and a tip positioned distal of the distal end of the recovery catheter. A mechanically radially expandable and contractible recovery device has a proximal end secured to the distal portion of the actuator sheath by a proximal extension element and a distal end secured to the tip of the actuator wire by a distal extension element. The recovery device comprises proximal and distal toroidal blocking balloons at the proximal and distal ends thereof, a central portion between the proximal and distal blocking portions, and a return lumen extending between the proximal and distal ends. The recovery device is placeable in a first, radially collapsed configuration when (1) the blocking balloons are in deflated states, and (2) the actuator wire is pushed distally to a distal actuator wire position relative to the recovery device and the actuator sheath is pulled proximally to a proximal actuator sheath position relative to the recovery device. The recovery device is placeable in a second, radially expanded configuration when (1) the blocking balloons are in inflated states, and (2) the actuator wire is pulled proximally to a proximal actuator wire position relative to the recovery device and the actuator sheath is pushed distally to a distal actuator sheath position relative to the recovery device. When in the second, radially expanded configuration (1) the proximal and distal blocking balloons have radial dimensions greater than the radial dimension of the central portion thereby defining a collection chamber at the central portion, and (2) the proximal and distal expansion elements have open regions to permit fluid flow through the return lumen of the recovery device. A lateral passageway extends through the central portion of the recovery device and the sidewall of the recovery catheter. The parts of the proximal and distal blocking portions and the central portion defining the collection chamber are liquid impervious with the exception of the passageway. Whereby liquid from an ostium of a liquid transporting vessel opening into the collection chamber can pass through the passageway and into and through the recovery lumen.

An example of a method for directing a fluid, which passes through an ostium into a body passageway, to a fluid recovery device is carried out as follows. A radially expandable and contractible recovery device is positioned within a body passageway at an ostium with the recovery device in a first, radially collapsed configuration, the recovery device having a proximal end and a distal end. The recovery device is placed in a second, radially expanded configuration, the placing step carried out at least in part by the mechanical manipulation of at least one mechanical actuator element thereby mechanically expanding the proximal and distal blocking portions so that when the recovery device is in the second, radially expanded configuration. The proximal and distal blocking portions have radial dimensions greater than the radial dimension of the central portion thereby at least partially defining a collection chamber at the central portion. Fluid from the collection chamber is directed into the recovery device. In some examples the radially expanded configuration placing step is carried out using first and second mechanical actuator elements operably coupled to proximal and distal ends of the recovery device. In some examples the radially expanded configuration placing step is carried out completely by the mechanical manipulation of the at least one actuator element. In some examples the radially expanded configuration placing step further comprises inflating proximal and distal toroidal blocking balloons at the proximal and distal ends of the recovery device.

An example of a method for recovering venous effluent from an organ, the organ having a distal vein and a draining vein, is carried out as follows. A funnel device of a recovery catheter assembly is placed within a tubular body vessel at a venous ostium of an organ being treated, the funnel device having an open end. The open end of the funnel device is placed within the distal vein of the organ at the ostium. The funnel device is forced against the venous wall to create a seal between the funnel device and the draining vein thereby creating a collection chamber defined between the funnel device and the organ. An agent is infused into the patient. Fluid from the organ is collected in the collection chamber. The collected fluid is filtered. The filtered collected fluid is returned to the patient.

An example of a method for determining the effectiveness of a seal at a collection chamber created between a recovery device of a recovery catheter assembly and an organ from which fluid is collected is carried out as follows. An indicator agent and a therapeutic agent are infused into a patient. A fluid, which passes through an ostium of an organ into a body passageway, is collected in a collection chamber defined between a fluid recovery device of a recovery catheter assembly and the organ. The collected fluid is processed. The processing step comprises removing the indicator agent and the therapeutic agent from the collected fluid. The processed fluid is returned to the patient. Systemic fluid is collected from the patient. The collected systemic fluid is tested for the presence of the indicator agent.

An example of a method for removing a therapeutic agent from a patient is carried out as follows. A therapeutic is infused agent into a patient. A fluid passing from an organ is collected. A binding material comprising an affinity agent is added into the collected fluid. The therapeutic agent within the collected fluid is bound to the affinity agent. The collected fluid and the binding material are processed. The processing step comprises removing the binding material with the therapeutic agent bound thereto from the collected fluid. The processed fluid is returned to the patient.

Other features, aspects and advantages of the present invention can be seen on review the figures, the detailed description, and the claims which follow.

BRIEF DESCRIPTION OF THE DRAWINGS

FIGS. 4-8 are illustrated examples of recovery catheter assembly including mechanically assisted expansion mechanisms made according to the present invention FIG. 4 shows a first example of a mechanically assisted expansion apparatus made according to the invention.

FIG. 6 illustrates an alternative to the example of FIG. 4 including toroidal balloons used in conjunction with the mechanically assisted expansion mechanism.

FIG. 7 illustrates a further alternative similar to that of FIG. 6 using obliqued toroidal balloons.

FIG. 8 shows an alternative example similar to that of FIG. 6 in which the pump and filter are placed in extended section of recovery catheter.

FIGS. 9-16 show other examples of recovery catheter assemblies.

FIG. 9 shows a recovery device including a funnel catheter.

FIGS. 11A, 11B and 11C show a retrievable temporary balloon expandable strut in three different states.

FIG. 12 is a cross-sectional view taken along line 7-7 of FIG. 11C.

FIGS. 14, 15 and 16 show additional examples of retrievable isolation apparatus.

DESCRIPTION OF THE EXEMPLARY EMBODIMENTS

Figure 1:
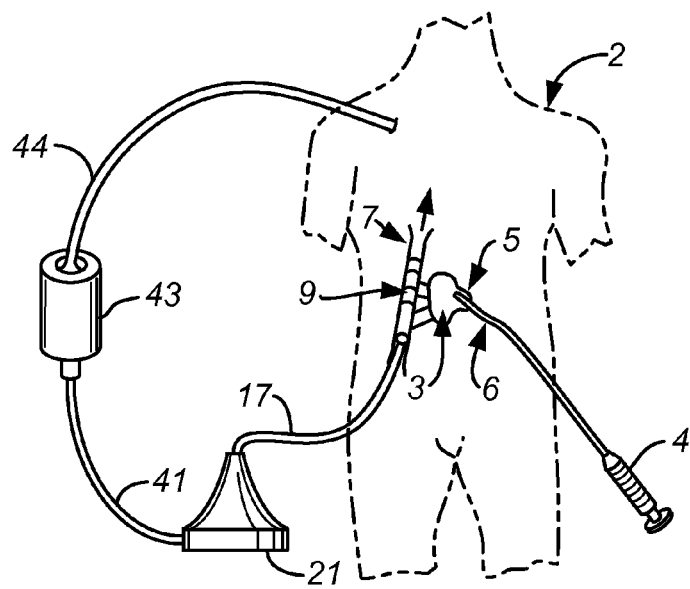
FIG. 1 shows a patient being treated with a prior art isolation apparatus.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows Like elements in various embodiments are commonly referred to with like reference numerals.

FIG. 1 is a representation of a patient 2 being treated with a prior art apparatus. The drug or substance is injected by a syringe 4 or pump (not shown) into the hepatic artery 5 and perfuses the liver 3. The hepatic venous effluent is collected by the double balloon catheter 9 in the upper inferior vena cava 7 and directed into the connecting tubing 17 to the pump 21, then to the filter 43 via the connecting tubing 41 between pump 21 and filter 43, and then the filtered blood is transported back into the patient's 2 systemic circulation by connecting tubing 44 returning blood to the internal jugular vein.

Figure 2:
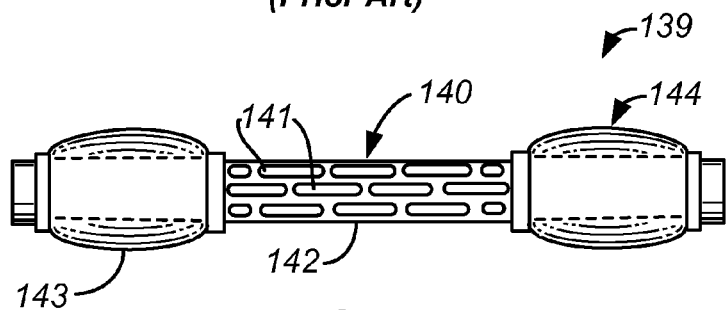
FIG. 2 shows a prior art isolation apparatus with the balloons in deflated states.

FIG. 2 is a prior art isolation apparatus 139 demonstrating the uninflated balloons 143, 144 and the holes 141 in the external catheter 140 through which the hepatic venous effluent flows into an external situated lumen. The return channel or through lumen (not shown) that transmits the inferior vena caval blood to the right atrium is in a central lumen (not shown) which is necessarily smaller than needed as the catheter 142 must contain the recovery lumen for the hepatic venous effluent, inflation channels for the balloons, and the through return lumen for IVC blood to pass to the right atrium.

Figure 3:
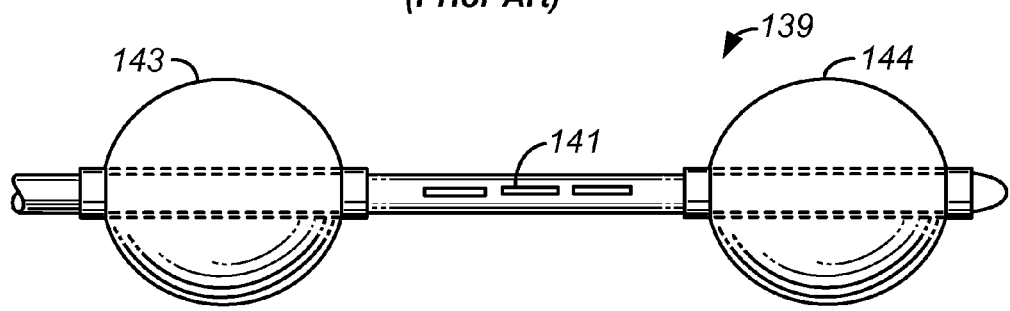
FIG. 3 shows the prior art apparatus of FIG. 2 with the balloons in inflated states.

FIG. 3 is the prior art apparatus 139 with the balloons 143 and 144 expanded so that the section of inferior vena cava (not shown) between the balloons 143 and 144 is isolated. The caudal balloon 143 is placed below the most caudal hepatic veins (not shown) and the cephalic balloon 144 is placed near the juncture of the inferior vena cava (not shown) and the right atrium (not shown). Blood flowing out of the hepatic veins into this section of isolated inferior vena cava is collected through the openings 141 in the wall of the catheter into an external lumen and transported via tubing 17, 41, 44 to the pump 21 and filter 43 and then back into the body 2 as in FIG. 1. There is central channel (not shown) that serves as the return through channel to transport the blood from the IVC to the right atrium. Because of the external collection channel of the isolation apparatus, two balloon inflation channels and the walls of these channels, the central return through channel has an inadequate annular space to transport sufficient blood from the IVC to the right atrium. This constriction is necessary because of the design of the prior art device, and, as mentioned above, is problematic. Moreover, one can easily see that the footprint of the expanded balloons 143, 144 is so large that other vital veins may easily be inadvertently occluded. The current invention will obviate these problems in one of several configurations described henceforth.

Ideally, the device of the present invention should be relatively small for easy insertion, and then expand in the inferior vena cava to function, then contract to a small size again for removal. In fact, while the above descriptions of the different embodiments have discussed the use of materials that are expansile, expansible, self expanding, balloon expansible, self contracting, and so forth, it is the inventor's conclusion that after the review of the CT scans on 50 patients that the wide variety of size and shapes of the inferior vena cava, the critical length needed to cover the hepatic venous ostia but not occlude the adrenal and renal veins, the need for a small footprint caudally, and the need for an adequate through return lumen places unusual demands on a device which cannot be met by simply applying prior art techniques (self expanding, balloon expandable, etc.) that may have been used elsewhere in the vascular system to a hepatic venous effluent recovery catheter. Hence, one preferred embodiment as discussed below with reference to FIGS. 4 and 5A-5C, as well as the other embodiments, will function best with a system of mechanically assisted expansion, which utilizes a mechanism proximally (for example outer actuator sheath 73) and a mechanism distally (for example actuator rod 154) that will provide additional tension on the proximal and distal flares 131, 132 to enhance and assist the expansion and contraction of them. While several of the embodiments utilize balloon expansion and one embodiment utilizes a self expanding braid, a presently preferred configuration is one that uses a non balloon, mechanically assisted expansion, such as recovery device 138 of FIGS. 4 and 5A-5C.

The reasons that mechanically assisted expansion will work better than a self expanding design in the inferior vena cava include the following.

1. Foreshortening: With self expansion there will be a significant amount of foreshortening upon expansion of the device, and the amount of foreshortening will depend on the size and shape of the IVC. If the diameter of the IVC is small, there will be less foreshortening than if it is large. There is a need to cover all of the hepatic veins (which typically range from 6.5-7 cm top to bottom), but not to occlude adrenal or renal veins. Therefore the length of the device when deployed is critical. One generally does not have control over the length with a self expanding device and this may result in the occlusion of the renal and adrenal veins. Alternatively, one could control the length with a mechanically assisted expansion, as one could adjust the tension on the flares (flares 131, 132 discussed below with reference to FIG. 4) to match the anatomy present in the individual patient. Hence, in a patient with a small IVC, one would increase the tension on the flares creating less length than would be present without this added mechanical assistance, adding an element of control not present with a purely self expanding system. This reason alone provides a strong incentive for not using self expanding only designs and using a mechanical assisted expansion design.

2. To be effective at all, a self expanding braid must be oversized and the elastomeric membrane applied in the oversized state, less the membrane will cause the braid to contract. When one attempts to remove the self expanding device (typically approximately 45 mm fully distended in oversized state) through a 15 Fr. (5 mm) catheter, one will have to deal with the extra membrane material which will become irregularly folded and clumped when the braid is contracted. This is especially true when removing the distal annular flare as the center portion of the braid is attached to the recovery tubing and not allowed to contract fully by proximal tension on the braid. In other words, one may be able to remove the proximal annular flare and the center portion by traction on the braid, but one should expect difficulty in removing the distal annular flare which has been oversized purposefully with excess membrane material in a self expanding configuration. Mechanically assisted expansion and contraction would obviate this problem.

3. A self expanding tubular mesh braid typically exerts less radial force than a laser cut stent (which would be extremely expensive), therefore one may need a mechanical assisted expansion to create a tight seal, i.e., extra radial tension force not present with self expansion, especially considering the many different shapes and angles in the inferior vena cava. In fact, the acute angle present in the immediate suprarenal inferior vena cava that was frequently demonstrated on the CT study mentioned above would cause particular problems for a self expanding device as there would be inadequate seating of the braid because of the acute angle at this location, and hence inadequate sealing of the device. One would need active expansion, i.e., mechanical assistance, to drive the braid with more force than would be possible with a purely self expanding system.

4. Tradeoff in wire sizes and number of wires: The device can be made more compact with fewer and smaller wires, but will have less radial force and lesser chance of creating a tight seal if only self expansion is utilized. A compact device can be constructed if there is mechanical assisted expansion to provide for a secure seal.

5. As detailed later, the presence of the recovery catheter attached only to the ventral aspect of the braid in FIG. 4 will tend to cause the recovery catheter to be centered in the vessel when it is actually eccentrically placed. The use of a self expanding mechanism may cause unequal pressures against the IVC wall by the flares, especially given the varying shapes of the IVC, and hence the potential for a less than secure seal. The use of a mechanical assist mechanism would provide for additional annular tension that would overcome this potential problem.

6. Another property of tubular braided structures is that there is a critical braid angle that needs to be achieved to provide radial strength. When this critical angle is achieved the braided tube becomes stronger and the inward force required to collapse the braid dramatically increases. This critical angle of the braid is more readily achievable with an active expansion, or mechanically assisted expansion, that would tend to drive the braid to a larger diameter than would be possible with a purely self expanding system. In fact, the critical angle that does give the braided structure its optimal braid angle and hence optimal radial strength may not be achievable at all with a purely self expanding device. Moreover, even if this critical braid angle were achieved with a purely self expanding system, collapsing the braid for retrieval may be even more problematic.

7. A self expanding system needs an outer sheath to constrain the device for insertion and retrieval. With an active system to control the expansion and contraction of the device, this outer sheath may not be needed creating an overall smaller size profile than would be achievable with a purely self expanding system.

The reasons a mechanically assisted expansion mechanism as described subsequently in FIGS. 4-8 will work better than a balloon-only expanded mechanism as demonstrated in some of the current embodiments in prior art devices are:

1. Obviating the use of the balloon makes the device simpler.

2. The balloon-only assisted expansion may not provide the force needed to create a tight seal or control the length when the balloon is deflated to allow IVC blood to return to the heart.

3. In some situations balloon expansion mechanism may be used in conjunction with a mechanical assisted expansion, and some of the current embodiments reflect this.

Hence, for the reasons listed above, the novel mechanically assisted expansion of the current invention is superior to previously described stand alone techniques and methods such as balloon-alone expansion and self expansion. As used in this application, mechanically assisted expansion is carried out with mechanical expansion structure with or without the use of a balloon to assist expansion in the preferred embodiments.

One preferred embodiment of a recovery catheter assembly 136 is shown in FIGS. 4-4B and 5A-5C, and includes a recovery device 138 using an expandable or expansible and collapsible mesh braid 130 with an elastomeric covering 97. Although it may be self expanding, self contracting, it is preferably expansible by mechanical expansion structure which will be described subsequently.

The recovery device 138 in this configuration has a "dog bone" configuration with the protruding flares 131, 132 on each end creating the blocking element that define the extent of the hepatic venous effluent collection chamber 94 (HVECC) covering the ostia 51 of hepatic veins 52. Braiding techniques, heat treating of the nitinol (or other material from which the braid 130 is made), the attachment of the braid 130 to the recovery catheter 76, defining a recovery lumen, and possible lay-ins in the braid will determine the shape of the device 138. The mesh braid 130 of the device 138 is covered with or coated with an elastomeric substance 97 in all but its proximal and distal ends creating a modified cylindrical channel within the tubular mesh braid 130. The elastomeric covering, typically of a silicone composition or some other biocompatible material that is resistant to degradation by the chemotherapy, or other, agent, may extend proximal to the proximal flare 131 and distal to the distal flare 132, but would not cover the ends of the device 138. This will allow a very generous through return channel 124 for blood to flow from the lower IVC lumen 99 into the right atrium (not shown.)

The expanding structure 100 may be made of a mesh braid, laser cut materials, or any other generally tubular, radially expandable mechanical structures that can be expanded into a more or less tubular configuration that would allow an adequate through channel for IVC blood to return to the right atrium without much impendence or obstruction. The present invention is also directed to methods of using generally tubular, radially expandable mechanical structure to convey IVC blood from an area near the renal veins to the supradiaphragmatic IVC or the right atrium while collecting hepatic venous effluent, and all devices which would facilitate such a method with or without the extracorporeal filtration system described above and elsewhere.

In the preferred embodiments of FIGS. 4-8, the expanding structure 100 is expanded by means of a proximal actuator sheath 73 and a distal actuator wire 154 attached to a proximal wire set 146 and to a distal wire set 147 of the mesh braid 130, respectively. By exerting forward pressure upon the outer actuator sheath 73 with respect to the recovery lumen 76, the proximal flare 131 will expand to the wall of the inferior vena cava creating a seal and providing expansion of the proximal portion 124 of the through return channel 124 defined between actuator shaft 73 and the elastomeric coated mesh braid 130. By exerting a pulling pressure on the actuator wire 154, the distal flare 132 will expand to the wall of the inferior vena cava creating the distal seal and providing the expansion of the distal portion of the through return channel 124. The hepatic venous effluent collection chamber 94 is created between these two flared ends of the device. In addition to creating collection chamber 94, the mechanically expanding structure 100 also creates the return channel 124, discussed in more detail below.

The recovery catheter 76 that collects blood and the chemotherapeutic agent from the HVECC 94 and transfers it to the extracorporeal pump (not shown) is bonded to the ventral surface of the coated expandable mesh braid 130. At least one hole 95, and preferably several holes 95, are placed through the braid 130 and material 97 covering the braid and into the lumen 68 of the recovery catheter 76. See FIGS. 5A-5C. This allows communication of the lumen 68 of the recovery catheter 76 with the HVECC 94 and the hepatic venous effluent would flow from the HVECC 94 through the holes 95 and into the recovery catheter 76, and then be transported extracorporeally to be filtered before being returned to the body.

The bonding of the catheter to the braided structure is of special concern as this may be a potential point of failure. A simple circumferential bonding (not shown) around the hole through the wall of the braided device 130 and the holes 95 in the recovery catheter 76 may suffice, but it is anticipated that a broad area bonding (not shown) of the surface of the catheter to the braided structure, as well as a focal circumferential bonding, may be needed and would provide an extra degree of safety. Other members (not shown), such as wires, may be utilized to encircle the recovery catheter 76 and engage the coated mesh braid structure 130 to fix the recovery catheter to the mesh braid structure, in addition to the bonding described above. Prevention of leakage of the toxic hepatic venous effluent into the systemic circulation is a high priority.

Since the coated braided structure 130 is bonded to the recovery catheter 76 in the more or less mid portion of the braided structure 130, collapsing of the braid will be more difficult than if it were not bonded, in that the proximal mechanism will not collapse the distal aspect of the braided structure. Therefore, in this particular embodiment, a second collapsing mechanism is supplied in the form of a stiff push/pull rod or actuator wire 154 that occupies a channel 69, see FIGS. 5A-5C, within the wall of the recovery catheter 76. The distal wire set 147 of the braided structure 130 is attached to this rod or wire 154 by crimping, soldering, or by other appropriate means. Retracting the wire 154 will cause the braided structure 130 to expand against the vessel wall 155 and form a seal 156 about the HVECC 94 that will be created. Advancing the wire/rod 154 will cause the braided structure 130 to collapse for insertion and removal. The proximal portion 131 of the braided structure 130 will be expanded and collapsed by the movement of the actuator sheath 73 with respect to the recovery catheter 76.

Figure 4:
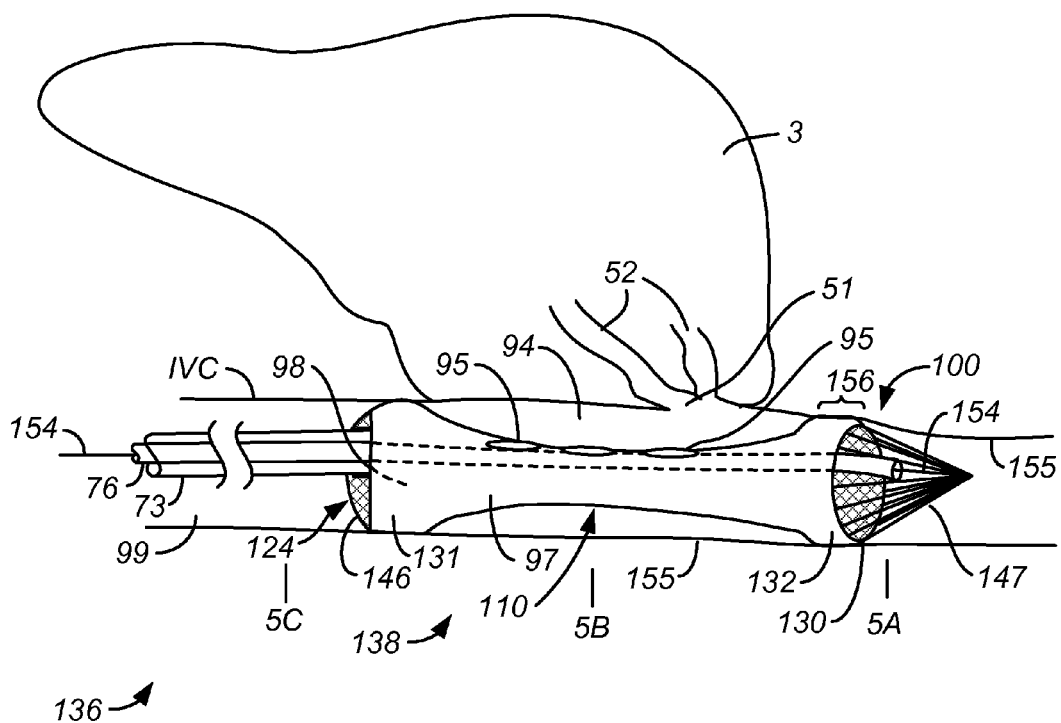
Figure 4A:
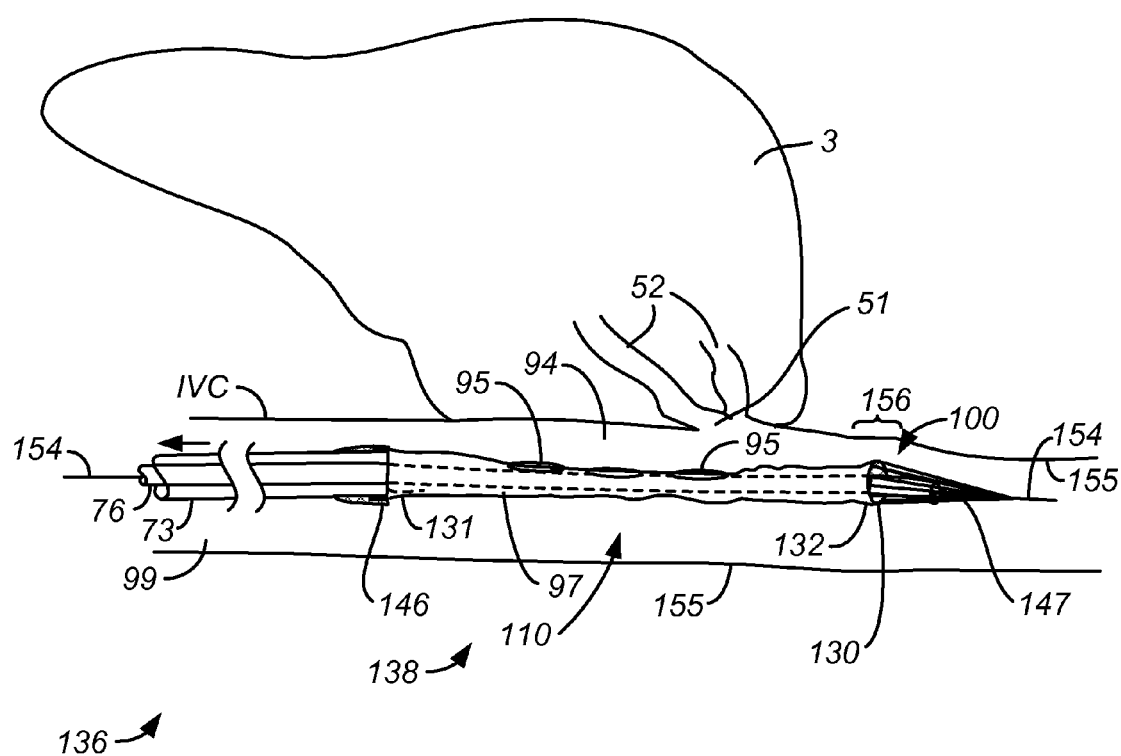
FIG. 4A shows the structure of FIG. 4 in a collapsed state.
Figure 4B:
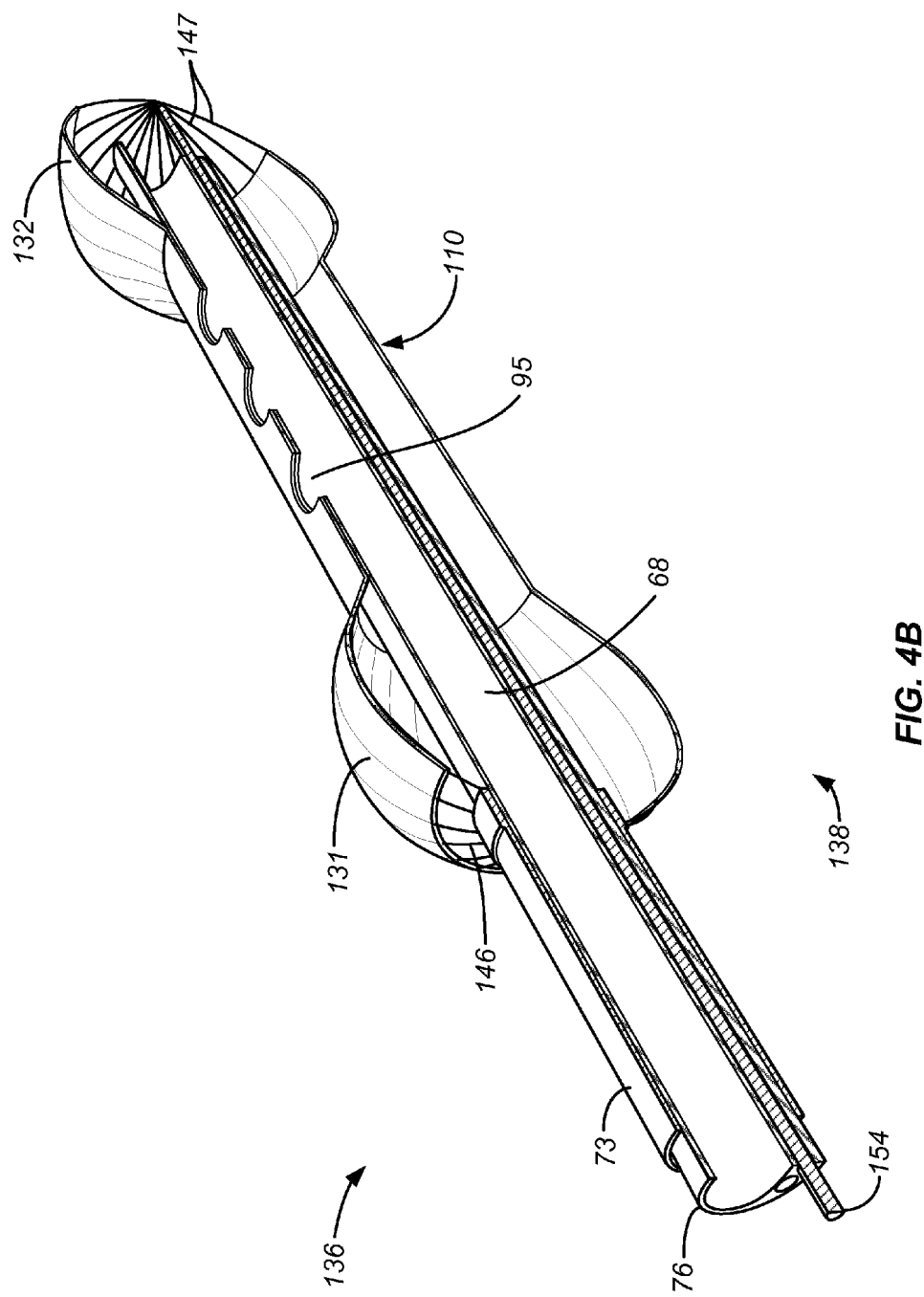
FIG. 4B is a cross-sectional perspective view of the structure of FIG. 4.

Of special note is the eccentric nature of the recovery catheter 76 in FIGS. 4 and 4A. The braid 130 attached proximally to actuator sheath 73 through proximal wire set 146 will tend to center the recovery catheter 76 in the lumen 99 of the blood vessel IVC. Ideally, the recovery catheter 76 needs to remain eccentrically placed with in the lumen 99 of the vessel to maintain as large as possible return channel 124 for the blood to flow unimpeded. The braid may not provide equal pressure against the vessel wall 155 at the flared ends 131, 132 because of the eccentricity and this may contribute to unequal sealing of the HVECC 94. These negative features may be partially overcome by different braiding techniques, heat set techniques, and additional lay-ins for braid 130 amongst other techniques. Additionally, the members of the braid 130, that is the proximal wire set 146, attached to actuator sheath 73 would be shorter on the ventral aspect of the device which may help resolve this difficulty somewhat, and the distal wire set 147 of braid 130 is attached to the distal tensioner wire 154 which is indeed centered within the blood vessel lumen 99. In other words, the attachment of the proximal braid 146 to the actuator sheath 73 in such a manner that forward pressure on the actuator sheath will provide annular radial force to the proximal flare 131 may be essential to providing a tight seal against the wall of the IVC. Without this added pressure, the eccentric nature of the flare 131 may prevent equal or adequate pressure against the IVC wall 155, especially since the size and shape of the IVC is so varied from patient to patient and even within the same patient.

Figures 6, 7:
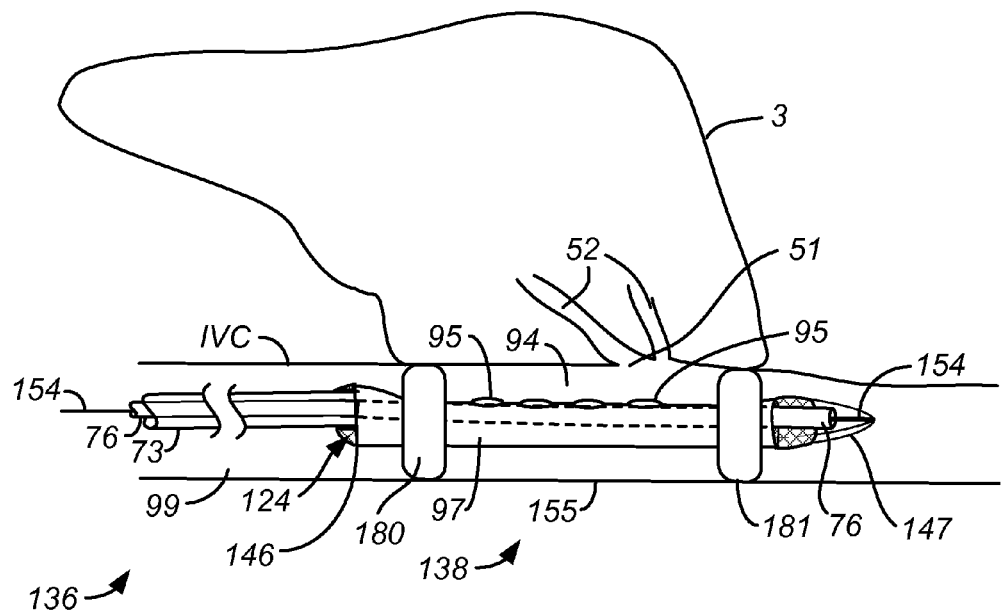

Even another alternative embodiment as shown in FIG. 6 utilizes a mechanically assisted expansion device as shown in FIG. 4, but the mechanically assistance is utilized only to expand the return channel 124. The HVECC 94 is defined by balloons 180, 181, which may be toroidal balloons, on the proximal and distal ends of the through return channel 124. The presence of the mechanically assisted expansion apparatus will overcome many of the problems inherent in a self expanding device that are listed herein and allow easier placement and repositioning, easier deployment and, more importantly, easier recovery of the tubular recovery device 138. The mechanically assisted expansion will also allow more pressure to be exerted radially and prevent collapse of the return channel 124 when the balloons 180, 181 are inflated. The balloons, being more flexible than the braided flares 131, 132 of other embodiments, will conform to the acute angles within the inferior vena cava better than the braided wire structures and provide for a more consistent and predictable seal. There has been no problem with leakage of the prior art device that is currently in use which utilizes balloons. The balloons function well to contain the hepatic venous effluent. The problem with the prior art device is that the balloons are too large and occlude the renal and adrenal veins in some cases, and that the through return channel is too small to convey a sufficient volume of blood from the kidneys and lower body via the inferior vena cava to the heart. This latter problem causes the patient to go into shock, as well as a myriad of other problems, enumerated previously. Hence, the balloons are not the problem with the currently used prior art device, it is the size of the balloons and the size of the through return lumen that is problematic. These deficiencies are addressed with various embodiments, including those of FIGS. 6 and 7.

The braided tubular structure is covered with an impermeable and elastic substance 97 that is resistant to chemotherapeutic compounds as the prior embodiments. It is essentially tubular rather than having the flares 131, 132 or expanded ends as present in FIG. 4. The tubular structure representing the return lumen 124 is attached to an inner, recovery catheter 76 which communicates with the hepatic venous effluent collection chamber (HVECC) 94 via one or more apertures 95. An outer actuator sheath 73 is slideable relative to the inner recovery catheter 76 to assist with expansion and collapse of the tubular return channel 124. The braid 130 is attached to this recovery catheter 76 so that tension can be provided to expand the braid, or to assist with the expansion of the braid, by advancing the outer actuator sheath 73 with respect to the inner, recovery catheter 76, and tension can be provided to collapse the braid, or assist with collapsing the braid more completely, by withdrawing the outer sheath 73 with respect to the inner catheter 76.

A stiff push wire or actuator wire 154 may be attached to the distal wire set 147 to expand or collapse, or assist the expansion or collapse of the tubular braided structure as previously illustrated in FIG. 4. Expansion or assistance with expansion is accomplished by withdrawing the wire 154 with respect to the inner, recovery catheter 76. Collapse or assistance with collapse of the tubular braided through return channel 124 is accomplished by advancing the wire 154 with respect to the inner catheter 76. The wire 154 preferably is housed within a lumen 69 of the wall of the inner catheter 76 as per FIGS. 5A, 5B, and 5C.

Figure 5A:
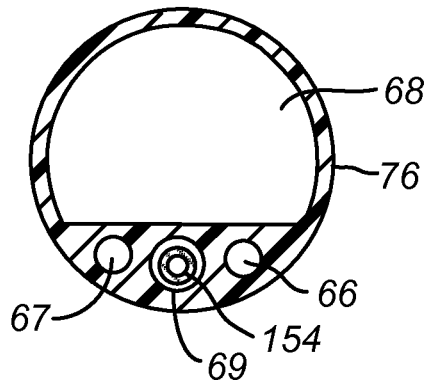
FIGS. 5A, 5B and 5C are cross-sectional views taken along lines 5A-5A, 5B-5B and 5C-5C in FIG. 4, respectively.
Figure 5B:
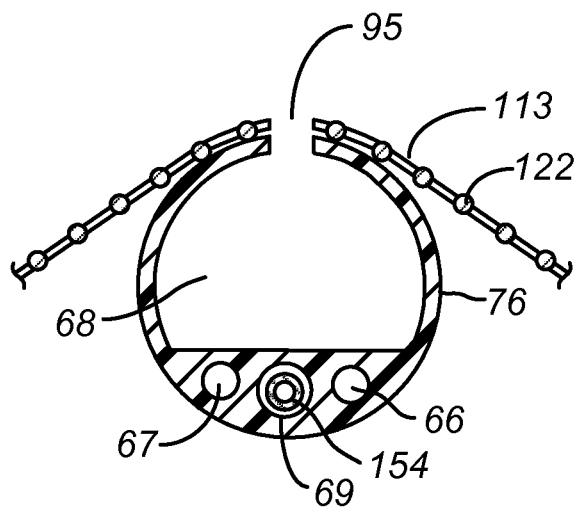
Figure 5C:
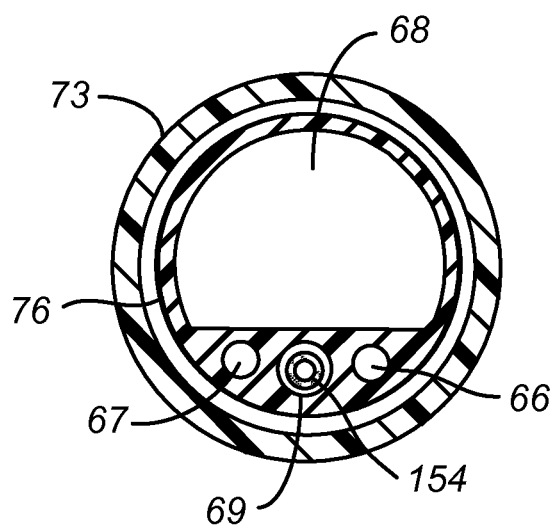

The proximal balloon and the distal balloons are attached to the outer surface of the tubular braided through return lumen and are inflated via inflation lumens 66, 67 as pictured in FIGS. 5A, 5B, and 5C, although the inflation lumens may be positioned differently within the wall of the inner catheter 76 than shown in these illustrations. These two balloons 180, 181 are oriented more or less perpendicular to the expandable through return channel 124 and encircle the expandable through return lumen 124 with a toroidal shape. The most cephalic positioned balloon 181 may be larger than the more caudal balloon 180 as it may be advantageous to seat the cephalic end of the device and the cephalic balloon in the right atrium. The portion of the inferior vena cava between the right atrium and the hepatic veins 52 is typically larger than the suprarenal inferior vena cava (as was determined from the CT study performed by the inventor mentioned above), hence the need to provide a larger balloon or other sealing device cephalically. Since both the proximal and distal balloons are oriented more or less perpendicular to the axis of the through return lumen, the footprint is much smaller than the spherical balloon of the current prior art device, and therefore occlusion of the adrenal and renal veins will not be nearly as problematic as with the current prior art device.

Alternatively, the elastomeric covering 97 may cover only a portion of the mesh braid as was will be discussed in FIG. 14. If this were the case, a balloon structure (not shown) would essentially encircle or surround the HVECC 94 to define it rather than the two toroidal balloons 180, 181 of FIG. 6.

Moreover, the CT study demonstrated that the left renal vein 182 (in FIG. 7, which is a view of the device in the IVC from an anterior or coronal perspective) was always positioned more cephalically than the right renal vein 183. It also demonstrated that accessory hepatic veins 184 enter the IVC either ventrally or on the right side. Hence, it may be advantageous to position the caudal toroidal balloon 180 at an angle as shown in FIG. 7 so that the HVECC 94 extends more caudally on the right to avoid occluding the accessory hepatic veins 184 and capture the accessory hepatic venous effluent from HVECC 94, but more cephalically on the left to provide a safety margin against the inadvertent occlusion of the left renal vein 182 which can be positioned at nearly the same axial level as the most caudal accessory hepatic vein 184. Additionally, the cavoatrial junction is also frequently asymmetrical, and obliqued balloons may be utilized at both ends to better accommodate the unique anatomy present in the proximal and suprarenal IVC. Using an obliqued toroidal balloon 810 in FIG. 7 overcomes the need for the proximal and distal occlusion mechanisms, whether expandable braid or spherical balloons, to be symmetric when there is in reality a non symmetric anatomy present.

Figure 8:
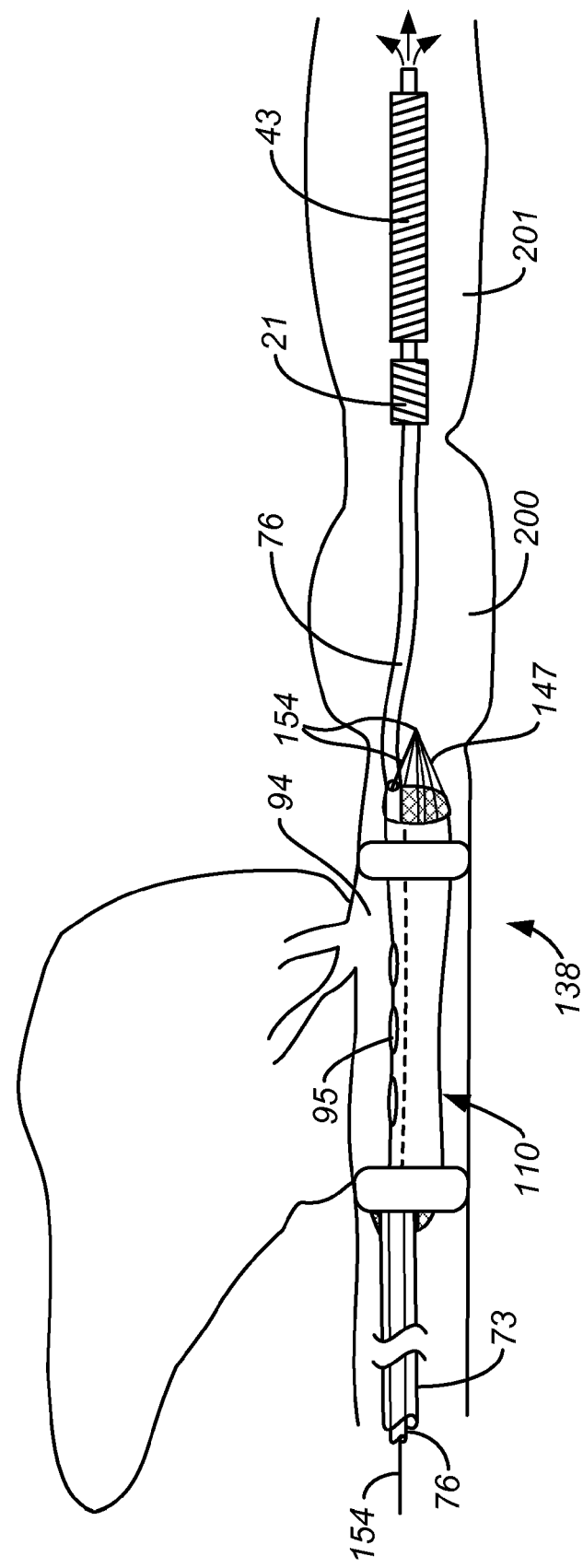

The presence of the pump and filter outside of the body is inconvenient and creates additional steps as well. Placing the pump and filter within the recovery catheter and returning the filtered blood to the systemic circulation without transporting it to an extracorporeal location may be accomplished by miniaturizing the pumping and filtering components. FIG. 8 shows a simplified view of a recovery catheter 76 similar to FIG. 6 with the filter 43 and the pump 21 present within an extended section of the catheter 76. This extended section traverses the right atrium 200 and into the superior vena cava 201. The presence of the pump 21 in close proximity to the hepatic venous effluent collection area 94 has the added benefit of creating a negative pressure region within the hepatic venous effluent collection area 94, further guarding against any leak into the systemic circulation, as if there is lower pressure in the hepatic venous effluent collection 94 area than in the IVC 99, there would be no chance of leakage into the higher pressure of the IVC. The pump 21 may be one of three general types of pumps that are able to propel blood, i.e., roller, centrifugal, and axial pumps. Of these types, a centrifugal pump may likely be best suited for this application as they generally cause less hemolysis than the other types, and can be more easily miniaturized. Centrifugal pumps consist of a nonocclusive pump head and various numbers of impeller blades positioned within a valveless pump housing usually powered electromagnetically. Pump rotation generates a vortex resulting in nonpulsatile unidirectional blood flow and high flow rates can be achieved, although the centrifugal pumps can bridge a limited pressure differential. In the intended use within this invention, there is venous to venous flow which does not demand a significant pressure differential. Several companies currently produce centrifugal pumps including Medtronic, Sarns, and St. Jude Medical, amongst others. Pumps developed for neonatal use may be modified for use in the current application. Axial pumps consist of a rotor type impeller housed in a small casing and mechanical action is powered by an electromagnetically powered rotor system. An example is the Impella pump from Impella Cardiotechnik AG, or even the MicroMed DeBakey VAD. The pump 21 only may be placed in the catheter in another embodiment (not shown) with the filter 43 remaining extracorporeal.

The filter 43 for the example of FIG. 8 may be any one of several types including but not limited to electronic, cartridge, membrane, microtubular, microfluidic, magnetic, chemical, activated carbon, positively or negatively charged filter components, and others. The filter element can be produced from any suitable media such as carbon based or synthetic media which can extract a drug from blood by adsorption or binding drug molecules to porous structures, anion exchange, particulate filtration, aggregate filtration and so forth. Filter structures can be hollow fiber membrane, semi permeable membrane, granular media, woven or non woven filter fabrics or other suitable forms. The filter may be expandable (not shown) after it has been inserted especially if the efficiency of the filter is dependent on the surface area of the filter, preferably in the superior vena cava 201 or right atrium 200 allowing the filtered blood to be returned to the superior vena cava 201 or right atrium 201 without being transported extracorporeally. In the case of an activated carbon filter, the absorption efficacy may be different for several different types, i.e., ROX, UKR, CLA, amongst others, of activated carbon as well as shape and surface morphology. The particles may be coated with a polymethyl methacrylate copolymer, or some other material, at different thicknesses and with different methods to diminish the effect on red blood cells and other blood components. Frequently there may be a trade off between coating thickness and absorption efficiency. Another type of filter that may be used is one that contains porous hollow fibers which may be coated with affinity agents, or the affinity agents may be either within or outside the hollow fibers. The blood can be pumped either through the porous hollow fibers, and the substance to be removed is selectively transported to the space outside the hollow fibers, or conversely, the blood may be pumped through the spaces outside the fibers and the substance to be removed is selectively transported to the interior of the hollow fibers.

Another type of blood filter is a microfluidic blood filter. Used with the current device, the chemotherapeutic agent would be infused and collected as previously described in FIG. 8, but upon entering the recovery lumen 76 the blood containing the chemotherapeutic agent would be admixed with coated iron oxide beads that are coated with an affinity agent. The chemotherapeutic agent would adhere to the coated beads and be pumped with the blood through to the filter 43 where an electromagnet (not shown) would separate the beads and chemotherapeutic agent from the blood. Given the space restraints of an in-catheter filter, this system has advantages as it may obviate the bulk required by traditional designs. A hybrid filter may also be used which employs one or more of the different filter types within the same device.

The filter 43 may be expanded by the pressure of the pump 21, or by other means. The blood from the hepatic venous effluent chamber 94 would enter the recovery catheter 76 via apertures 95 as in several other embodiments and proceed cephalically in the extended segment of the recovery lumen 76, through the pump 21 and the filter 43 and exit into the superior vena cava 201 or right atrium 200 through the distal end of the device. A side hole 203 may be provided in the recovery catheter 76 for the exit of the stiff actuator rod 154. Alternatively the actuator rod 154 may be attached to a separate actuator sleeve (not shown) located exterior to the recovery catheter 76 that is attached to the tubular braid in this location and would be slideable relative to the recovery catheter 76, so that retraction of the actuator rod 154 would move the separate actuator sleeve (not shown) to expand the braid and advancement of the actuator rod 154 would move the separate actuator sleeve (not shown) to collapse the braid.

Even another embodiment (not shown) utilizes a self expanding return channel 124, and toroidal shaped balloons 180, 181 as in FIG. 6, but without the active expansion system as in FIGS. 6 and 7. While the active mechanical expansion assistance provides a control not found in purely self expanding systems, the expansion assistance provided by inflating the balloons combined with a self expanding mechanism of the through return lumen may provide enough radial strength to maintain patency of the through return lumen in this embodiment. The sealing function will be provided by the balloons, hence some of the objectionable qualities of a self expanding system listed previously are not as pertinent if the self expanding component is just the through return lumen as is the case in this particular embodiment. The function and components of this embodiment are otherwise essentially the same as in FIGS. 6 and 7.

Other Recovery Catheter Assemblies

Figure 9:
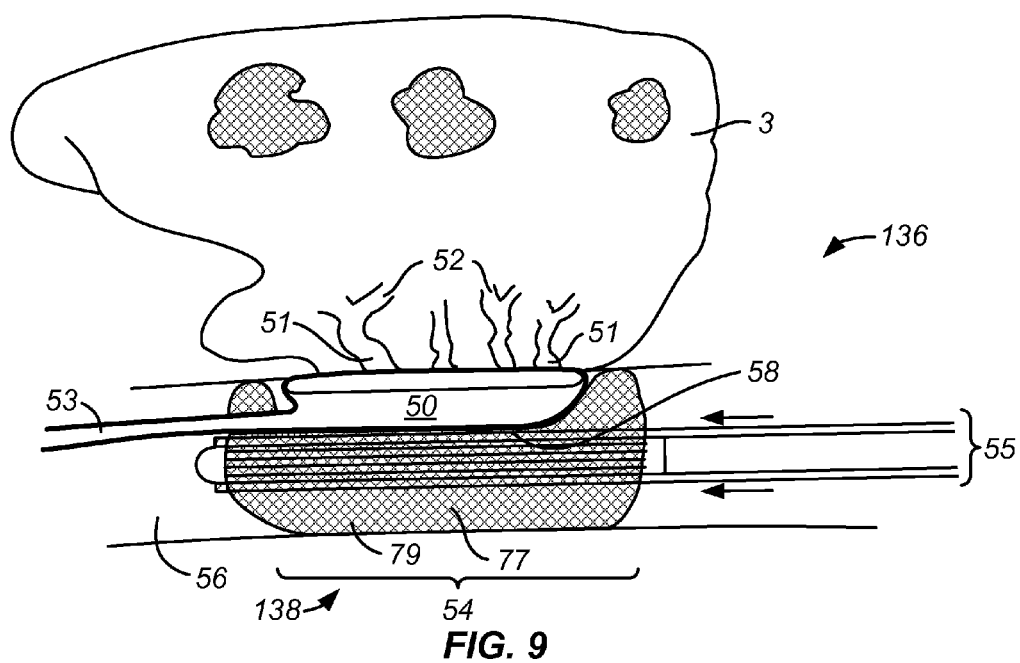

FIG. 9 shows another example of a recovery catheter assembly 136 including a recovery device 138. Recovery device 138 includes a funnel catheter 50 that covers the ostia 51 of the hepatic veins 52, isolates the hepatic venous effluent and retrieves the hepatic venous blood into the catheter 53 or tubing to be pumped into the filter 43 and returned to the body as in FIG. 1. The funnel catheter 50 is held in place by a temporary retrievable balloon expandable strut 54 provided on a separate venous catheter 55 securing it over the hepatic venous ostia 51. Balloon expandable strut 54 includes a mesh of struts 77 defining an open architecture 79. The length of temporary retrievable strut 54 is longer than the funnel catheter 50 by design as this will further secure the ends of the funnel catheter to the ventral inferior vena cava 56. The strut 54 also compresses the periphery of the funnel 50 assuring a tight seal against the ventral aspect of the inferior vena cava 56. The surface of the strut 54 compressing the funnel 50 may be indented or have a concavity 58 so as to not obstruct the funnel 50. The open architecture 79 of the strut 54 will not obstruct venous inflow from the renal or adrenal vein even if it covered them. This design solves the two problems of the prior art device mentioned above, the occlusion of renal/adrenal veins and the lack of an adequate through return channel for IVC blood. The temporary strut 54 forces the funnel catheter 50 (which is obliquely shaped) against the ventral aspect of the proximal IVC 56 securing it over the hepatic venous ostia 51 without occluding renal/adrenal veins. The funnel catheter 50 occupies very little annular space in the IVC 56 allowing blood to flow freely from the mid and distal IVC 56 into the right atrium through the spaces or interstices 59 in the temporary strut 54 when the balloon 60 on the temporary strut 54 is deflated.

Figure 10A:
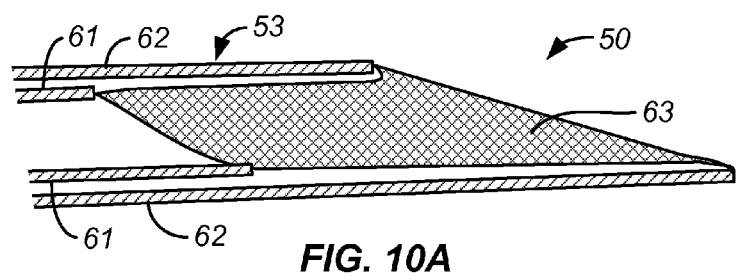
FIGS. 10A and 10B show the funnel catheter of FIG. 9 in more detail.
Figure 10B:
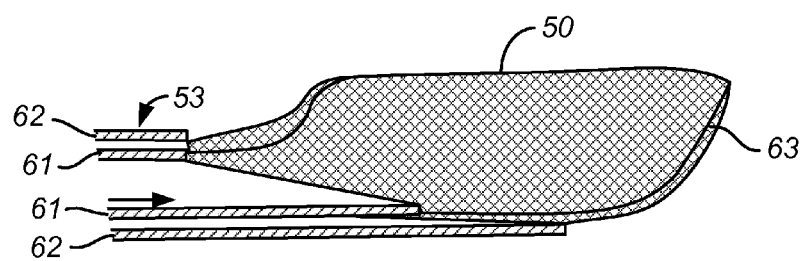

FIGS. 10A and 10B demonstrates the funnel catheter 50 in more detail. It is composed of two shafts 61, 62 and a mesh braid 63 of nitinol (or other appropriate biocompatible material) covered with a silicone elastomer (not shown) or other substance that is expansible and resistant to degradation by the chemotherapeutic agent. Unique to this application, however, the two shafts 61, 62 of the funnel catheter 50 are obliquely angled at their distal ends 64 so that the funnel 50 projects to the side of the catheter rather than directed distally in the prior art funnel catheters. In FIG. 10A, the inner shaft 61 is retracted in respect to the outer shaft 62. This keeps the mesh braid 63 of the funnel 50 within the lumen of the outer shaft 62. The mesh braid 63 is bonded to both the inner shaft 61 and to the outer shaft 62. As the inner shaft 61 is retracted, the mesh braid 63 forms a cylindrical channel parallel and within the channel formed by the outer shaft 62. As demonstrated in 10B, when the inner shaft 61 is advanced distally toward the ends of both shafts, the mesh braid 63 is propelled out the distal end of the outer shaft 62 and forms a funnel 50. Moreover, the shape and the strength of the funnel catheter 50 can be affected by adding longitudinal, horizontal, and oblique lay ins. The shape memory properties of nitinol and the ability to place these lay ins with specific properties at specific locations within the braid allows a braid configured device to be tailored to the specific application. The combination of nitinol combined with brading technology essentially assures that most any shape is possible. In fact the description in this paragraph of forming a shape to cover the hepatic vein orifices is different than previous methods, which are all a funnels projecting distal to the end of the catheter. This construction may be used in other examples discussed herein.

FIGS. 11A, 11B, and 11C represent the retrievable temporary balloon expandable strut (RTBES) 54. In FIG. 11A, the strut 54 is expanded over the inflated balloon 71. The catheter contains two shafts, and outer one 73 and an inner one 76. The balloon is attached to the inner shaft 76 and the RTBES 54 is attached to the outer shaft 73 via a bond 77. Distal to the balloon 71 the braid 77 of the strut 72 is bonded 69 to the inner shaft 76 as shown.

FIG. 11B demonstrate the balloon 71 to be deflated while the strut 54 is expanded. Forward force (arrows) on the outer shaft 73 with respect to the inner shaft 76 will assist in keeping the strut 54 expanded against the wall of the IVC (not shown) and the funnel catheter (not shown.) The interstices 79 of the strut 54 provide more than adequate space for blood to flow from the IVC into the right atrium. The pressure from the strut 54 forces the funnel catheter 50 against the ventral IVC and secures it in place over the hepatic venous ostia 51. The RTBES 54 may be inserted via the internal jugular vein or the femoral vein, as may the funnel catheter, but usually the two would be inserted through separate veins. Moreover, the shaft 76 of the RTBES 54 may be utilized as the return conduit after the hepatic venous blood has passed through the filter, as it would serve no other purpose while the hepatic infusion was being performed. If utilized in this manner, it would be preferentially inserted via the internal jugular vein. Additionally, the shafts 73, 76 of the RTBES 54 may have openings (not shown) into the lumen along the shafts 73, 76 so some of the returning blood would be directed into the superior vena cava.

In FIG. 11C, the outer shaft 73 is retracted (arrows) with respect to the inner shaft 76 collapsing the strut 54 over the balloon 71, as the outer shaft 73 is bonded 77 to the strut 54 proximally and the inner shaft 76 is bonded 69 to the strut 54 distally. This will allow insertion and removal of the device 55 in a low profile.

FIG. 12 is a cross section of the two shafts 73, 76 of the device 55 proximal to the balloon 71 and strut 54. It demonstrates the inner shaft 76 and outer shaft 73. The inner shaft 76 comprises a large lumen 68 and at least one smaller lumen 67 for inflation of the balloon. Another lumen 66 may be present for insertion of a guide wire (not shown) or for injection of contrast. Contrast may be injected also through the space 65 between the inner shaft 76 and outer shaft 73.

Figure 13A:
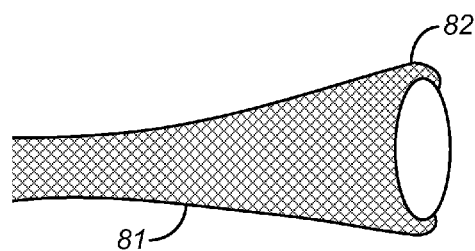
FIG. 13A shows a funnel catheter.
Figure 13B:
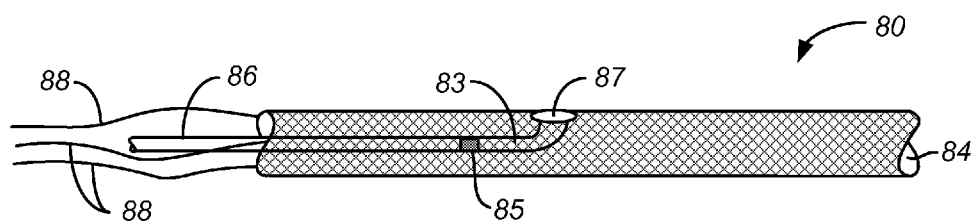
FIG. 13B shows a retrievable isolation apparatus including an expandable mesh grade structure.
Figure 13C:
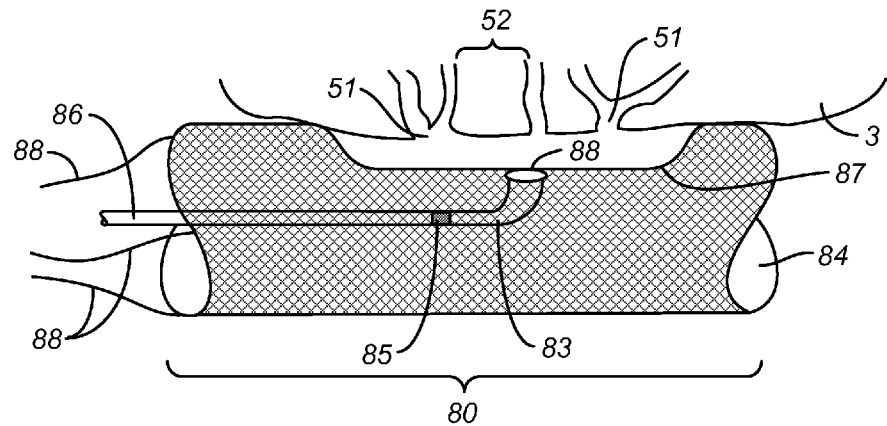
FIG. 13C shows the structure of FIG. 13B in use.

FIGS. 13B and 13C discloses a retrievable self expanding or balloon expandable mesh braid structure 80. It may be delivered and retrieved through a funnel catheter 81, see FIG. 13A, which is likely to be dissimilar to the funnel catheter 50 in FIG. 10. The funnel catheter 81 may be a simpler design in that occlusion or isolation is not required of the funnel catheter in this configuration and the funnel 82 at the distal end of the catheter is directed along the axis of the shaft of the catheter. The funnel catheter may not be even needed in fact.

In FIG. 13B, the isolation apparatus is a retrievable self expanding or balloon expandable mesh braid structure 80 covered with an elastomeric material (not shown) resistant to the chemical properties of concentrated chemotherapeutic agents, such as, but not limited to silicone. The elastomeric covering (not shown) may cover all of this tubular structure 80, or, in a preferred embodiment, only the ventral half. This latter configuration would preclude obstruction of renal or adrenal veins. In this particular configuration, the isolation chamber apparatus is a tubular mesh braid structure 80 with a side arm 83 that is inverted into the main lumen 84 of the structure 80. This inverted side arm 83 is bonded 85 to the recovery tubing 86 that transports the hepatic venous effluent to the exterior of the body where it is pumped through the filter. Alternatively, the recovery tubing 86 may be attached similar to the recovery lumen 76 of FIG. 4. Also shown are the tether wires 88 attached to the structure 80 so that it may be withdrawn into the funnel catheter 81 for removal. Instead of the inverted side arm, the mesh braid structure 80 may be alternatively attached to the recovery lumen 83 as demonstrated above in FIG. 4.

As shown in FIG. 13C, the ventral aspect of the retrievable tubular structure 80 containing the inverted side arm 83 contains a concavity 87 large enough to cover the ostia 51 of the hepatic veins 52 as well as to serve as a small reservoir to direct the hepatic venous effluent through an orifice 88 into the inverted side arm 83 and the recovery tubing 86 to the exterior. This configuration provides effective hepatic venous isolation as well as a very generous through return channel for IVC blood to pass to the right atrium, solving the major problems of the prior art device.

Figure 14:
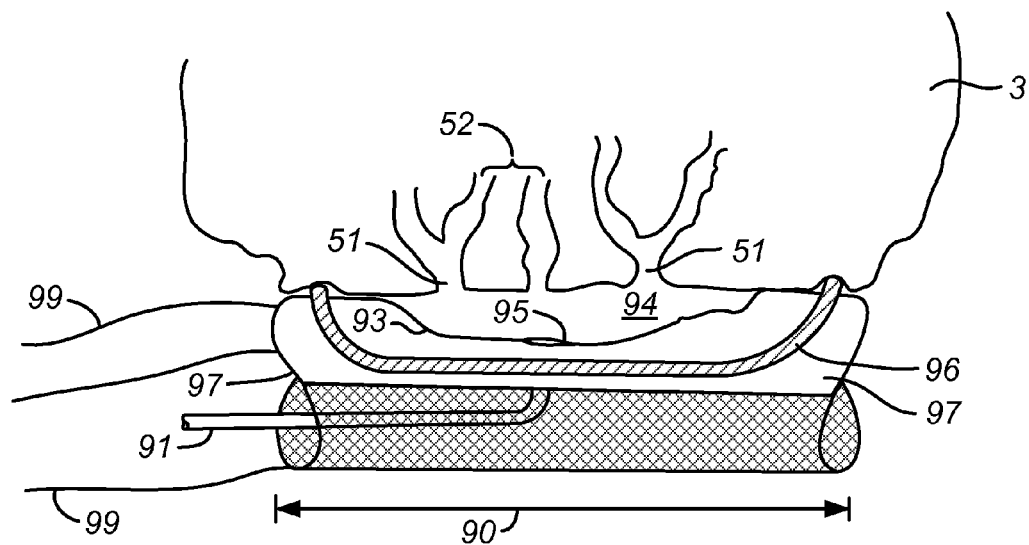

FIG. 14 demonstrates a retrievable isolation apparatus 90 in which the tubing 91 to the exterior is bonded (not shown) directly to the wall of the apparatus 90 vs. the more flexible inverted side arm 83 as in FIG. 12. The wall of the retrievable isolation apparatus 90 has a concavity 93 that covers the hepatic venous ostia 51 and serves as a small reservoir 94 to direct blood into the tubing 91 through an orifice 95. The other properties are similar to those in FIGS. 8B and 8C. In both inventions of FIGS. 8B, 8C and 9, there may be provided additional layer or layers of the elastomeric material 96, or even a balloon structure (not shown), about the collection chamber to enhance the seal. A special braiding technique of the braid (not shown) may also enhance the seal at these locations. Since the hepatic veins enter the IVC either ventrally or on the right side, the elastomeric coating may be limited to these locations rather than being circumferential. Additionally, in the examples of the devices in FIGS. 8 and 9 in which the elastomeric material 97 covers only the ventral and right side aspect of the apparatus, the additional sealing method 96 described above may essentially encircle the concavity described above to provide more effective sealing. The tether wires 99 are also shown.

Additionally the expandable mesh braid with the elastomeric coating 97 may contain a funnel shaped structure (not shown) on both ends to provide isolation of the hepatic venous blood. The ends may be comprised of a self expanding material (not shown) such as Nitinol that would cause the ends to flare out and contact the IVC wall with an exaggerated amount of force to provide an extra sealing property.

Figure 15:
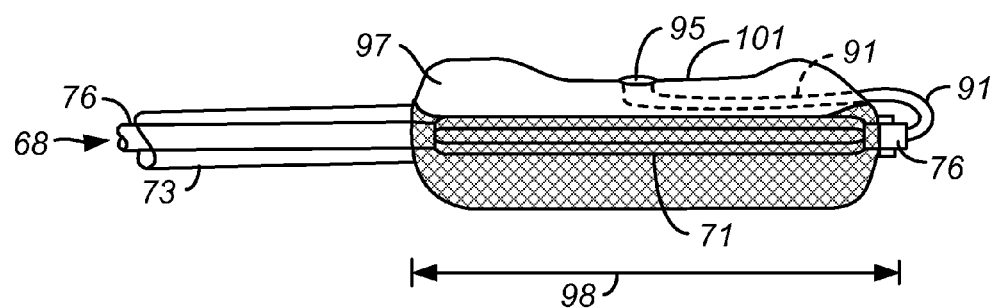

FIG. 15 demonstrates another configuration which is similar in construction to FIGS. 11A, 11B and 11C in that a retrievable temporary balloon expandable strut (RTBES) 98 is utilized. However the RTBES 98 is not utilized to compress the funnel catheter 50 against the ventral aspect of the IVC in this particular configuration. The RTBES 98 contains the collection chamber 101 which functions as the funnel catheter 50 did in the prior example. This RTBES 98 expands by inflating a balloon 71 and contracts by manipulating the inner shaft 76 and outer shaft 73 as demonstrated in FIGS. 6A, 6B, and 6C. At least the ventral aspect of the strut 98 is covered with an elastomeric material 97, although the elastomeric material may cover all of the structure except for the distal and proximal ends, and may have an extra layer 96 of elastomeric material at least partly encircling the collection chamber 94, as in FIG. 14. The shape of this and other configurations can be controlled by braiding technology, the use of lay ins, and so forth. The hepatic venous collection tubing 91 may be directed extracorporeal as in the prior examples, but may alternatively be directed to and bonded to the distal aspect of the inner lumen 76 as is shown. The cross sectional view of FIG. 12 would apply in this instance and the hepatic venous blood would be directed through the large central lumen 68.

Figure 16:
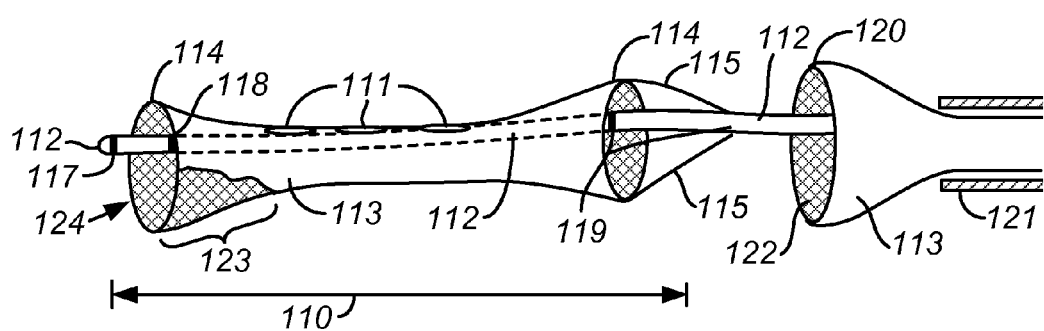

FIG. 16 demonstrates even another configuration in which a retrievable self expanding mesh braid device 110 with an elastomeric covering 113 is utilized. This double funnel 114 configuration in which the ends 114 of the device 110 flare out more than the central section. The central portion of the device 110 would be bonded to the recovery catheter 112 with at least one, but preferably several orifices 111 in the recovery catheter 112. The added pressure at the ends would create an effective seal, isolating the hepatic venous effluent and directing it into the orifices 111 connecting to the recovery catheter 112. Tether wires 115 on the proximal end of the device 110 may be attached to the shaft of the recovery catheter 112 or may be bonded together to form a single tether wire (not shown) for removal of the device 110. In this example, the recovery catheter 112 extends through the entire length of the device 110 to give some rigidity and pushability to the device for placement, manipulation, and removal purposes. It may not extend the entire length of the device 110 however.

The braiding technique will typically create more expansile braid at the ends of the structure and less expandability in the central portion. Welds of the filaments in the center of the braid may be utilized to create a center section that is smaller than the distal ends as may the insertion of horizontal lay ins.

The bonding of the orifices 114 in the ventral aspect of the device 110 will also help create a small reservoir in the central portion for the hepatic venous effluent. The funnel shaped ends will have a smaller footprint than the expanded balloons in FIGS. 1, 2, and 3 prior art devices, and should not occlude the renal veins. However, about the dorsal aspect of the distal end of the device 110, a section of braid 123 may not be coated with the elastomeric coating 113. This would allow blood from renal or adrenal veins to flow into the return through channel 124 through the open mesh.

There may or may not be radiopaque markers at the end 117 of the recovery catheter 112, the distal end of the device 118, and the proximal end 119 of the device 110. Alternatively markers (not shown) may be on the device 110.

The device 110 will typically be delivered and removed through a funnel catheter 120 which is a mesh braid 122 with an elastomeric coating 113 housed within a outer sheath 121. In deployment the outer sheath 121 containing all of the components above would be inserted in the femoral or internal jugular vein and, in the case of the internal jugular vein insertion, the tip positioned just below the most caudal hepatic vein. While keeping forward pressure on the recovery catheter 112, the outer sheath and the funnel catheter 120 would be withdrawn together deploying the device 110 as shown in FIG. 16. The proximal end would be cephalic to the most cephalic hepatic veins. The hepatic artery would be infused with a selected agent, and hepatic venous blood collected in the recovery catheter 112 through the orifices 114 and pumped through the filter outside of the body, and returned to the body as in FIG. 1. Alternatively, the filtered blood may be returned to the body through the funnel catheter 120. At the termination of the procedure, the outer sheath 121 would be withdrawn from over the funnel catheter 120 exposing the funnel 120. The device 110 then would be withdrawn through the funnel catheter 120 by withdrawing the recovery catheter 112. When the device 110 was within the funnel 120, the funnel 120 containing the device 110 would be withdrawn into the outer sheath 121, and the entire apparatus removed. Again a generous through return lumen has been provided, an effective collection chamber is present, and means are provided to prevent occlusion of the renal and adrenal veins.

Even another configuration of this apparatus (not shown) utilizes an expandable funnel to occlude the IVC caudal to the most caudal hepatic veins similar to FIG. 16 and a balloon to occlude the upper IVC just below the right atrium. In other words, the flare 114 of FIG. 16 may be present on the caudal end, that is to the left, in FIG. 16, and a balloon structure (not shown) may be present on the cephalic end. The central lumen which serves as the return through channel to return IVC blood to the right atrium may be a self expanding braided segment with an elastomeric coating that is similar to that of FIG. 16. The hepatic venous blood that flows into the hepatic venous collection tubing does not have a separate channel within the isolated segment as in the prior art devices of FIGS. 1, 2, and 3. The hepatic venous effluent collects in a space outside of the expandable through return channel and directed into the recovery catheter which is directed through the balloon on the cephalic end in one iteration. The balloon inflation lumen may be contained in the wall of the shaft of the hepatic venous collection tubing as previously discussed. The cephalic end of the central return lumen in the right atrium may have openings to allow the IVC blood to exit this central lumen or may be comprised of the mesh braid without the elastomeric coating, the IVC blood flowing through the interstices of the braid. In this configuration, the funnel distally will provide occlusion of the IVC and effective isolation of the hepatic venous segment of the IVC with a very small footprint, obviating occlusion of the renal and adrenal veins, while the combination of the funnel shape of the caudal orifice of the expandable segment of the through return channel combined with the expanded through return channel will provide a very adequate conduit for blood to flow freely from the IVC to the right atrium. This configuration is a viable alternative to the prior art devices. The use of a balloon recognizes the fact that while the funnel shaped occluders will perform better than balloon occluders in most instances because of several reasons including the instant on/instant off capabilities, the much smaller footprint, larger through lumens, etc., that there may indeed be a need at the junction of the IVC and the right atrium to occlude with a large footprint.

The above method also has the benefit of creating a moderate degree of obstruction in the upper IVC, which may create increased pressure in the IVC vs. the hepatic venous effluent collection area. Obviating the obstruction to the returning blood is one of the main goals of the current invention as too much obstruction will cause a drop in blood pressure, etc., as described above. However, creating a controlled moderate amount of obstruction may be desirable to increase the IVC pressure above that in the hepatic venous effluent collection area so as to prevent leakage of the hepatic venous effluent into the IVC. This could be accomplished by a balloon or by other means incorporated into the design of the device, for example a baffle type device that is controlled by the operator. Pressure sensors may be provided within the upper IVC and within the hepatic venous effluent collection chamber to monitor the pressures of the two areas with or without the baffle device. This would be accomplished by providing wires along the catheter shaft(s) or by utilizing wireless pressure sensors. In this particular configuration, it is imperative that the seal about the hepatic venous effluent collection chamber prevent leakage not only from that chamber into the IVC or systemic blood, but also from the IVC into that chamber.

It should be noted that the pressure sensors would detect the pressure of the hepatic venous effluent and at least one pressure reading in the IVC or right atrium. By connecting the pressure sensors to a controller and the controller to the extracorporeal pump, the pump could be regulated to always have a lesser pressure in the hepatic venous effluent than in the IVC. If the pressure in the hepatic venous effluent became close to the pressure in the IVC, or even exceeded the pressure in the IVC, then the controller would speed the pump so that more blood was withdrawn from the hepatic venous effluent collection chamber, thereby diminishing the pressure within that collection chamber to a level safely below that in the IVC. This would ensure that there could be no leakage of hepatic venous effluent (lower pressure) into the systemic IVC (higher pressure,) If there was any leakage at all, it would be from the IVC into the hepatic venous effluent collection chamber, and this would not be harmful. The adjustment of the pressure by controlling the speed and output of the pump could be done automatically with the controller, or alternatively with a manual adjustment of the pump speed by the operator or an assistant who is manually monitoring the pressures hepatic venous effluent collection chamber and the IVC and/or right atrium. Alternatively, the pump could be programmed to run at a speed, or regulated by the controller utilizing a single pressure sensor, that would effectively keep the pressure in the HVECC, either by direct measurement or by extrapolated measurement, less than 1-2 mm Hg (the normal pressure in the right atrium) or thereabouts. This would insure that the pressure in the HVECC was less than the pressure in the IVC/RA, and hence there could be no leakage from a lower pressure system into a higher pressure system. In some examples the pressure in the IVC is taken manually before the procedure so that there would be needed only one pressure sensor proximal to the pump to control the pump speed and keep the pressure at this sensor less than the IVC pressure determined at the beginning of the procedure.

Still another alternative method (not shown) utilizes two balloons as the occlusion elements, both caudally and cephalically, but the through return channel is expansile by means of a catheter as in FIGS. 11A, B, and C. This would take advantage of the proven occlusion features of the balloons, but the expansile through return channel would provide a channel large enough to return the IVC blood to the right atrium without the rather meager lumen of the current device. The struts on the catheter of FIGS. 11A, B, and C would compress the inner circumference and inner wall of the balloon outward creating more annular space and lumen within the central open area of the balloon. The hepatic venous effluent is collected in the space isolated by the two balloon occlusion elements, and then transported to the exterior of the body. This may be done by a separate catheter lumen or through the main lumen of the catheter of FIGS. 11A, B, and C.

A modified version of the embodiment (not shown) described in the above paragraph would utilize a self expanding apparatus to create the expansile through return channel within the center or "donut hole" of the balloons. It would be similar to the embodiment of the above paragraph, but the struts would expand without the use of a third balloon. The occluding balloons would be compressed from their inner circumference, enlarging it so as to provide an adequate through channel. A balloon configuration with an enlarged central channel has been termed a toroidal balloon. A toroidal balloon structure on each end of the device to define the limits of the hepatic venous effluent collection chamber (HVECC) may be combined with a self expandable structure such as a mesh braid or other self expandable structure and mounted on a catheter 73 as shown in FIG. 4 and FIG. 6. The balloons (not shown) would either augment or replace the flares 131, 132 in FIG. 4 or be placed as in FIG. 6 or FIG. 7. Otherwise this modified version would be generally similar to FIG. 6.

Another completely separate method of performing perfusion of an organ with a toxic substance and collecting the venous effluent, while providing for blood flow would be to utilize the prior art device or one similar that does not have an adequate through return lumen, but to add a second additional catheter system and, if necessary, a pump to transport blood from the lower IVC, or some other region, extracorporeally and then return it to the systemic circulation beyond the point of collecting the venous effluent, usually the superior vena cava. This would essentially create an extracorporeal bypass circuit and likely be functional, although problematic because of the added catheters, punctures, pump, equipment and so on. A special return catheter (not shown) may have two return lumens: one for the hepatic venous effluent which has been filtered and another for the systemic IVC blood which has been routed extracorporeally around the obstruction created by the use of the prior art type devices. This would obviate the need for two return catheters. The current inventions solve the problem of lack of an adequate through return channel without resorting to this relatively cumbersome method.

To prevent movement or migration of the device during infusion, an attachment mechanism (not shown) at or near the skin insertion site may be provided. It may vary in configuration from a suture attached to the tissues, to a clip at the skin level, to an anchoring device, or any other means of preventing movement of the catheter.

The methods of utilizing all of the above examples are quite similar. Imaging studies such as CT scans, MRI, or others are utilized to measure the distance between the most cepahalad placement of the flared blocking element, whether it be the cavoatrial junction or the supradiaphramatic IVC, and a point just above the renal veins. Measurements are also taken of the dimensions of the IVC. An appropriately sized recovery device, such as the device 138 of FIGS. 4-8 of the current invention is chosen. Typically, a catheter is placed in the hepatic proper artery from a femoral puncture for subsequent perfusion of the liver by a concentrated high dose substance. The device of the current invention, in one configuration or the other, is placed in the IVC and deployed so that the isolation apparatus covers the hepatic venous ostia. The more cephalic end of the device may be placed in the right atrium or in the supradiaphragmatic IVC which is normally 1-3 cm. in length. In the case of the flared configurations of some of the embodiments, the distal flares may abut more force radially against the wall of the supradiaphragmatic IVC and the sealing annular force directed toward the wall of the IVC than if the device were placed in the right atrium and traction on the device at the cavoatrial junction utilized to produce a seal. Testing is done to determine if the placement is appropriate by injection of contrast in a retrograde manner through the recovery catheter and into the HVECC, and demonstrating that there is no leakage from the isolated segment. Contrast is injected into the distal IVC to determine that there is good return through flow to the right atrium. Testing will also evaluate the status of the renal veins and adrenal veins, and the device adjusted to provide for flow from these veins. Hepatic venous effluent will be collected, and the hepatic arterial infusion will begin. The venous effluent will be pumped and filtered extracorporeally and returned to the body as in the prior art devices for a period of time. After the arterial infusion is complete the venous effluent collection and treatment will continue for a prescribed period to prevent any delayed washout of the concentrated high dose substance from the liver into the systemic circulation. After a period of time, the chosen device will then be collapsed, retracted, and removed from the body.

In the cases where the approach is done preferably from the internal jugular vein, it anticipated that flush injections of contrast through the filtered blood return catheter that would be present in the femoral vein would be done to roadmap the anatomy, and could be done simultaneously with the placement of the apparatus as the blood would flow centrally toward the heart. A side arm on this catheter would provide a means of injecting contrast while the filtered blood return flow is maintained. This would be valuable to monitor the placement of the apparatus during the procedure and is not feasible with the current prior art devices.

It should be noted that features of the particular configurations listed above may be used with other configurations interchangeably to provide a smaller footprint of the isolation chamber in the IVC and to provide for an adequate return through lumen for IVC blood to return to the right atrium. While the devices described here have particular use in the inferior vena cava, use elsewhere in the body is also anticipated. Moreover, while the recovery of hepatic venous effluent has been described, reversing the flow through the recovery catheter apparatus may be done to deliver a drug or drugs or other substances in a retrograde manner to the liver via the hepatic veins or other tissues.

While the above descriptions of the funnel catheter and the isolation apparatus and the through return lumen describe the use of mesh braid as the supporting and expandable component of the particular configuration, other options are to be covered by this patent application, such as cross linking, spiral support configurations, strut like configurations, more or less parallel wires or support members, non-parallel wires or support structures, folded configurations, circumferential balloons, partially circumferential balloons, spiral balloons, abutting structures, and others.

In the case of treatment of cancers, tumors, infections, or conditions involving other organs which may have only one or two or a few veins draining that organ, there may be no need to occlude the vena cava. The simple insertion of a funnel catheter directly into the ostium of the vein(s) of that particular organ would serve to collect and isolate the venous blood from that organ. The funnel catheter, whether constructed of mesh braid or other materials, is a simpler, easier, safer, more stable and quicker method of isolating and collecting the venous effluent than balloon based catheters, and occlusion of a vein for the collection and isolation of venous effluent by any funnel catheter is expressly covered in this patent application.

In fact, the perfusion of a focal anatomic area whether it be an extremity, abdominal, thoracic, cervical, or cranial area, or other soft tissue or bone area with any substance in a concentration that would cause toxic effects in other areas of the body, and collection of the substance with a system that either does not use a balloon or provides for a expandable through channel is part of this application. For example the substance could be an antibiotic to treat a focal infection, an anti-tumor drug, a thrombolytic agent to dissolve clot, a substance that converts vulnerable plaque to stable plaque, or dissolve plaque, stimulates cellular growth, retards cellular growth, relieves pain, causes tissue atrophy or cellular apoptosis, causes lipolysis, causes hair growth or loss, improves or alters hearing, vision, taste, smell, and touch senses and the like. For example, the focal area or organ could be the brain, salivary gland, thyroid gland, lymph nodes, soft tissue, lungs, heart, spine, bone, kidney, ovary uterus, breast, extremities, digestive tract, nasal area and sinuses, eyes, ears, ant throat.

The local perfusion of an area of tumor with a highly concentrated substance may indeed be the first line of treatment in the future for the treatment focal malignancies to shrink if not obliterate the tumor. Surgery could then be done on the much smaller tumor, if indeed there were any tumor left.

In the case of organs that have only one or two veins, or organs where the venous drainage may be approached by several catheters that are placed directly in the ostium or ostia, the funnel catheter 113 design shown in FIG. 16 may be utilized. Another design for a funnel catheter is shown in FIG. 13A. The highly concentrated substance would be perfused into the artery of the organ, and the funnel catheter used for recovery of the venous effluent. The venous effluent would be pumped through the filter and returned to the systemic circulation as previously discussed. The action of the funnel in this particular embodiment may be controlled by moving inner and outer actuator sheaths 61 and 62 as in FIGS. 10A and 10B. The ends of the two actuator sheaths 61, 62 are angled in FIGS. 10A and 10B causing the funnel in that illustration to project to one side. With actuator sheaths having ends that are not angled, the funnel will project straight ahead from the ends of the two actuator sheaths with a shape demonstrated in FIGS. 13A and 16. This will allow the funnel catheter to be placed within the ostium of the organ being treated. Because of the mechanical action of the funnel caused by the two actuator sheaths as in FIGS. 10A and 10B, the funnel will exert radial force against the wall of the vein just inside the ostium and the braid will further anchor the funnel within the vein.

Organs that would be amenable to this approach include the kidneys, pelvic organs, extremity, brain, lung, breast, and various abdominal organs by placing the funnel catheter in the portal vein, amongst others. The artery serving that organ would be catheterized and the substance infused. A catheter for collection of venous blood using a balloon on the end to occlude or block the vein in question works fairly well, although is not as stable as desired, mainly because of its spherical shape. Balloons tend to slide within the vessel, and there is a much greater probability of a balloon occlusion collection catheter to slide out of the venous ostium that there is of the funnel catheter described above. The mesh braid creates a slightly irregular surface on the funnel which resists slippage along the venous wall without damaging the intima.

Moreover, the shape of the funnel is advantageous for another reason. Typical balloon catheters have an opening at the end of the straight cylindrical catheter just distal to the balloon. The venous effluent must be withdrawn through this end hole, and since it is desirable to keep the pressure in the draining vein less than the vein it is draining into, suction will be applied by the pump creating suction within this recovery catheter. With a single end hole, there is the possibility of the suction not only creating turbulence and resulting hemolysis, but also the possibility of causing the vein wall to occlude the single end hole because of the suction. The funnel catheter overcomes these problems by providing a smooth transition from a large diameter vein into the much smaller catheter, minimizing turbulence and hemolysis, and obviating obstruction of the catheter by the suction. Additionally, in recovering venous effluent from these single vein organs, it is imperative that any drainage through collateral veins be minimized or completely eliminated. Many venous collaterals exist, but only flow when there is increased venous pressure within the organ for some reason or another. Hence, having a catheter that can maintain a good deal of suction to keep the venous pressure low in the effluent vein and the organ is important in preventing collateral flow around the recovery system and leakage into the systemic circulation.

Certainly, the effectiveness of the seal about the recovery device acting as an isolation apparatus is paramount to prevent high concentrations of a deleterious substance from entering the systemic circulation. Since the free hepatic venous pressure is only 1-5 mm Hg. greater than the pressure in the upper IVC or right atrium, the seal does not have to be the same as that which might occlude arterial flow with pressure differentials of 100-200 mm Hg. However, it is imperative that no leakage occurs from the hepatic venous effluent chamber into the IVC. Testing the effectiveness of the seal may require frequent injection of contrast agent which is time consuming and not very accurate. An alternative method of detecting any leakage of the toxic substance would be to develop a real time assay of the toxic substance, and test systemic blood periodically. Alternatively, a substance that is easily assayed could be injected with the toxic substance into the hepatic artery. It would then be collected with the hepatic venous effluent along with the toxic substance and transported externally, where a separate filter (in line with the filter that filters the toxic substance) or the same filter would filter the easily assayed substance out of the blood to be returned to the body. Therefore, assays of systemic blood of the easily assayed substance would determine if the seal about the isolation apparatus was functioning properly. The easily assayed substance is filtered out of the returning blood, so if there was any activity in the systemic circulation, then it would alert the attending physicians that there was a high probability of a leak of the toxic substances into the systemic circulation. The easily assayed substance may be have the properties of methemoglobin or carbon monoxide, or any other substance for which there is a simple, quick, and easy assay, and also be a substance that is easily filtered.

It is apparent that the materials comprising the device must possess flexible, expandable, contractible, amongst other, characteristics including the ability to conform to different shapes and sizes within the same patient with enough annular force to effect a complete seal. The variety of shapes encountered in the IVC are much more varied than in the typical artery which has a more or less round shape and usually consistent, although occasionally minimal tapering, diameter throughout the area being treated or manipulated. While the pressures needed to seal the HVECC are less than the arterial system certainly, the need for the device to conform to different sizes and shapes in the same patient is of great importance in constructing a device for use in the retrohepatic IVC. The construction of the different embodiments of the current invention will utilize designs, materials and techniques specifically adopted to venous use and different than those devices typically utilized in arteries.

Compared to prior art isolation apparatus, recovery device 138 can achieve a smaller footprint as well as a larger through return lumen. Some examples of recovery device 138 can be made with either an adjustable length or different length devices may be used.

Any and all patents, patent applications and printed publications referred to above are incorporated by reference.

Modifications and variations can be made to the disclosed embodiments and examples without departing from the subject of the invention as defined in the following claims. For example, while the above examples and embodiments use separate mechanical actuators to expand the proximal and distal blocking elements, in some cases a single mechanical actuator could be used to the same effect; one such mechanical actuator could be a balloon housed within the recovery device having enlarged proximal and distal ends when expanded.

What is claimed is:

1. A recovery catheter assembly comprising:
   a first actuator element;
   a second actuator element;
   a mechanically radially expandable and contractible recovery device operably connected to the first actuator element and the second actuator element, the recovery device having a proximal end operably connected to the first actuator element and a distal end operably connected to the second actuator element;
   the recovery device comprising:
   proximal and distal blocking portions at the proximal and distal ends thereof; and
   a central portion between the proximal and distal blocking portions;
   the recovery device at least partially placeable in a first, radially collapsed configuration and in a second, radially expanded configuration by manipulation of the first actuator element and the second actuator element so that when in the second, radially expanded configuration the proximal and distal blocking portions have radial dimensions greater than the radial dimension of the central portion thereby at least partially defining a collection chamber at the central portion, the manipulation of the first actuator element and the second actuator element comprises movement of the first actuator element and the second actuator element with respect to the recovery device.

2. The assembly according to claim 1, wherein the recovery device is fully placeable in the first, radially collapsed configuration, and in the second, radially expanded configuration, by manipulation of the first actuator element and the second actuator element.

3. The assembly according to claim 1, wherein the recovery device comprises a mesh braid.

4. The assembly according to claim 3, wherein the recovery device comprises a proximal wire set securing the proximal end to the distal portion of the first actuator element, and the proximal wire set comprises a plurality of radially and axially extending elements, said radially and axially extending elements being extensions of said mesh braid.

5. The assembly according to claim 3, wherein the recovery device comprises a proximal wire set, securing the proximal end to the distal portion of the first actuator element, and a distal wire set, securing the distal end to the proximal portion of the second actuator element, each of the proximal and distal wire sets comprises a plurality of radially and axially extending elements, said radially and axially extending elements being extensions of said mesh braid.

6. The assembly according to claim 3, wherein the collection chamber is defined by the proximal and distal blocking portions and the central portion comprises an elastomeric material on said mesh braid.

7. The assembly according to claim 1, wherein:
   the recovery device comprises proximal and distal toroidal blocking balloons at the proximal and distal ends of the recovery device;
   the recovery device is placeable in the first, radially collapsed configuration when (1) the blocking balloons are in deflated states, and (2) the first actuator element and the second actuator element are in a collapsed actuation state; and
   the recovery device is placeable in the second, radially expanded configuration when (1) the blocking balloons are in inflated states, and (2) the first actuator element and the second actuator element are in an expanded actuation state.

8. The assembly according to claim 1, further comprising:
   a hollow recovery catheter having a sidewall and defining a recovery lumen.

9. The assembly according to claim 8, further comprising:
   a lateral passageway extending through the central portion of the recovery device and the sidewall of the recovery catheter, the parts of the proximal and distal blocking portions and the central portion at least partially defining the collection chamber being liquid impervious with the exception of the passageway;
   whereby liquid in the collection chamber can pass through the passageway and into and through the recovery lumen.

10. The assembly according to claim 9, wherein:
    the recovery catheter comprises proximal, intermediate and distal portions;
    the lateral passageway is located along the intermediate portion of the recovery catheter;
    a blood pump located along the distal portion of the recovery catheter; and
    a filter element located along the distal portion of the recovery catheter for filtering out at least one agent from fluid flow through the recovery catheter lumen.

11. The assembly according to claim 8, further comprising:
    a first pressure sensor at the collection chamber;
    a second pressure sensor positioned distal of the recovery device;

a filter element and a pump operably coupled to the recovery catheter to pump fluid through the recovery catheter and filter fluid passing through the recovery catheter; and the pump operably coupled to the first and second pressure sensors to permit control of the pressure within the collection chamber during use.

12. The assembly according to claim 8, further comprising:

a filter element and a pump operably coupled to the recovery catheter to pump fluid through the recovery catheter and filter fluid passing through the recovery catheter;

a pressure sensor proximal to the pump; and the pump operably coupled to the pressure sensor to permit control of the pressure within the collection chamber during use.

13. The assembly according to claim 1, wherein the recovery device defines a return channel between the proximal and distal ends when in the second, radially expanded configuration.

14. The assembly according to claim 1, wherein:

the recovery device comprises proximal and distal toroidal blocking balloons at the proximal and distal ends of the recovery device;

the recovery device is placeable in the first, radially collapsed configuration when (1) the blocking balloons are in deflated states, and (2) the one or more actuator element are in a collapsed actuation state; and the recovery device is placeable in the second, radially expanded configuration when (1) the blocking balloons are in inflated states, and (2) the one or more actuator element are in an expanded actuation state.

\* \* \* \* \*